United States Patent
Medoff

(10) Patent No.: US 10,758,224 B2
(45) Date of Patent: Sep. 1, 2020

(54) SYSTEM AND METHOD CONTROLLING A RELATIONSHIP BETWEEN FIRST AND SECOND BODIES ON A PERSON

(71) Applicant: TriMed, Incorporated, Santa Clarita, CA (US)

(72) Inventor: Robert Medoff, Kailua, HI (US)

(73) Assignee: TRIMED, INCORPORATED, Santa Clara, CA (US)

(*) Notice: Subject to any disclaimer, the term of this patent is extended or adjusted under 35 U.S.C. 154(b) by 418 days.

(21) Appl. No.: 15/470,321

(22) Filed: Mar. 27, 2017

(65) Prior Publication Data

US 2018/0271522 A1  Sep. 27, 2018

(51) Int. Cl.
*A61B 17/04* (2006.01)
*A61B 17/56* (2006.01)
*A61B 17/06* (2006.01)

(52) U.S. Cl.
CPC .... *A61B 17/06166* (2013.01); *A61B 17/0401* (2013.01); *A61B 17/0487* (2013.01); *A61B 2017/0404* (2013.01); *A61B 2017/044* (2013.01); *A61B 2017/0409* (2013.01); *A61B 2017/0412* (2013.01); *A61B 2017/0414* (2013.01); *A61B 2017/0417* (2013.01); *A61B 2017/0445* (2013.01); *A61B 2017/0458* (2013.01); *A61B 2017/0474* (2013.01);
(Continued)

(58) Field of Classification Search
CPC ............ A61B 17/0401; A61B 17/0487; A61B 17/06166; A61B 2017/0475; A61B 2017/0477; A61B 2017/0496
See application file for complete search history.

(56) References Cited

U.S. PATENT DOCUMENTS

| | | |
|---|---|---|
| 3,409,014 A | 11/1968 | Shannon |
| 4,409,974 A | 10/1983 | Freedland |
| 5,178,629 A | 1/1993 | Kammerer |

(Continued)

FOREIGN PATENT DOCUMENTS

| | | |
|---|---|---|
| EP | 1568326 A1 | 8/2005 |
| EP | 2883518 A1 | 6/2015 |

OTHER PUBLICATIONS

Office Action dated Nov. 22, 2018 in Canadian Patent Application No. 2,988,047.

(Continued)

*Primary Examiner* — Diane D Yabut
*Assistant Examiner* — Majid Jamialahmadi
(74) *Attorney, Agent, or Firm* — Wood, Phillips, Katz, Clark & Mortimer

(57) ABSTRACT

A system for controlling a relationship between first and second bodies and made up of a suture assembly with at least a first suture configured to define a restrictable loop structure with the suture assembly in an operative state. At least first and second restrictable sub-loops cooperatively define a first loop that can be reduced in size to thereby produce a force on the first and second bodies that urges them towards each other. A first loop length has a first sliding portion with a second loop length having a second sliding portion. At least one knot extends around the first and second sliding portions. The first and second sliding portions, upon each being moved within the at least one knot in a tightening sliding direction, cause a size of a respective sub-loop to be reduced.

26 Claims, 27 Drawing Sheets

(52) U.S. Cl.
CPC ............... *A61B 2017/0475* (2013.01); *A61B 2017/0477* (2013.01); *A61B 2017/0496* (2013.01)

(56) References Cited

U.S. PATENT DOCUMENTS

| | | | |
|---|---|---|---|
| 5,234,444 A | 8/1993 | Christoudias | |
| 5,306,290 A | 4/1994 | Martins et al. | |
| 5,306,301 A | 4/1994 | Graf et al. | |
| 5,769,894 A | 6/1998 | Ferragamo | |
| 6,027,523 A | 2/2000 | Schmieding | |
| 6,056,752 A | 5/2000 | Roger | |
| 6,099,568 A | 8/2000 | Simonian et al. | |
| 6,319,271 B1 | 11/2001 | Schwartz et al. | |
| 6,533,802 B2 | 3/2003 | Bojarski et al. | |
| 6,569,186 B1 | 5/2003 | Winters et al. | |
| 7,235,091 B2 | 6/2007 | Thornes | |
| 7,455,683 B2 | 11/2008 | Geissler et al. | |
| 7,530,990 B2 | 5/2009 | Perriello et al. | |
| 7,594,923 B2 | 9/2009 | Fallin et al. | |
| 7,651,509 B2 | 1/2010 | Bojarski et al. | |
| 7,670,361 B2 | 3/2010 | Nesper et al. | |
| 7,713,285 B1 | 5/2010 | Stone et al. | |
| D626,231 S | 10/2010 | Perchik | |
| 7,875,057 B2 | 1/2011 | Cook et al. | |
| 7,875,058 B2 | 1/2011 | Holmes, Jr. | |
| 7,887,551 B2 | 2/2011 | Bojarski et al. | |
| 7,901,431 B2 | 3/2011 | Shurnas | |
| 8,048,130 B2 | 11/2011 | Nesper et al. | |
| 8,221,455 B2 | 7/2012 | Shurnas et al. | |
| 8,231,674 B2 | 7/2012 | Albertorio et al. | |
| 8,298,247 B2 | 10/2012 | Sterrett et al. | |
| 8,323,338 B2 | 12/2012 | LeBeau et al. | |
| 8,361,114 B2 | 1/2013 | Stone et al. | |
| 8,366,744 B2 | 2/2013 | Bojarski et al. | |
| 8,403,929 B2 | 3/2013 | Weisshaupt et al. | |
| 8,425,554 B2 | 4/2013 | Denove et al. | |
| 8,460,379 B2 | 6/2013 | Albertorio et al. | |
| 8,491,632 B2 | 7/2013 | Stone et al. | |
| 8,512,375 B2 | 8/2013 | Torrie et al. | |
| 8,591,578 B2 | 11/2013 | Albertorio et al. | |
| 8,623,051 B2 | 1/2014 | Bojarski et al. | |
| 8,628,573 B2 | 1/2014 | Roller et al. | |
| 8,721,683 B2 | 5/2014 | Graf | |
| 8,721,684 B2 | 5/2014 | Denham et al. | |
| 8,740,939 B2 | 6/2014 | Stone et al. | |
| 8,753,375 B2 | 6/2014 | Albertorio | |
| 8,771,315 B2 | 7/2014 | Lunn et al. | |
| 8,790,369 B2 | 7/2014 | Orphanos et al. | |
| 8,790,370 B2 | 7/2014 | Spenciner et al. | |
| 8,834,523 B2 | 9/2014 | Ferragamo et al. | |
| 8,840,645 B2 | 9/2014 | Denham et al. | |
| 8,864,797 B2 | 10/2014 | Justin et al. | |
| 8,888,815 B2 | 11/2014 | Holmes, Jr. | |
| 8,926,661 B2 | 1/2015 | Sikora et al. | |
| 8,926,662 B2 | 1/2015 | Perriello et al. | |
| 8,932,331 B2 | 1/2015 | Kaiser et al. | |
| 8,961,538 B2 | 2/2015 | Koogle, Jr. et al. | |
| 8,961,575 B2 | 2/2015 | Choinski | |
| 8,986,352 B2 | 3/2015 | Weisshaupt et al. | |
| 9,005,245 B2 | 4/2015 | Thornes et al. | |
| 9,101,461 B2 | 8/2015 | Albertorio et al. | |
| 9,179,950 B2 | 11/2015 | Zajac et al. | |
| 9,204,960 B2 | 12/2015 | Albertorio et al. | |
| 9,259,217 B2 | 2/2016 | Fritzinger et al. | |
| 9,314,234 B2 | 4/2016 | Hirotsuka et al. | |
| 9,421,007 B2 | 8/2016 | Brady et al. | |
| 9,433,407 B2 | 9/2016 | Fritzinger et al. | |
| 9,439,644 B2 | 9/2016 | Lizardi | |
| 9,492,200 B2 | 11/2016 | Sikora et al. | |
| 9,517,060 B2 | 12/2016 | Flint | |
| 2006/0282119 A1 | 12/2006 | Perchik | |
| 2011/0066185 A1 | 3/2011 | Wotton, III | |
| 2013/0123810 A1* | 5/2013 | Brown | A61B 17/04 606/144 |
| 2014/0309689 A1 | 10/2014 | Sikora | |
| 2015/0073477 A1 | 3/2015 | Holmes, Jr. | |
| 2016/0157851 A1* | 6/2016 | Spenciner | A61F 2/0811 606/232 |

OTHER PUBLICATIONS

"Invisiknot" Ankle Syndesmosis Repair Kit, www.smith-nephew.com/professional/products/all-products/invisiknot, Mar. 27, 2017.
Knotless TightRope® Syndesmosis Fixation—Surgical Technique, 2015, Arthrex Inc. in conjunction with Brian Thornes, M.D.
"JuggerKnot" Soft Anchor, 2011, Biomet Sports Medicine.

* cited by examiner

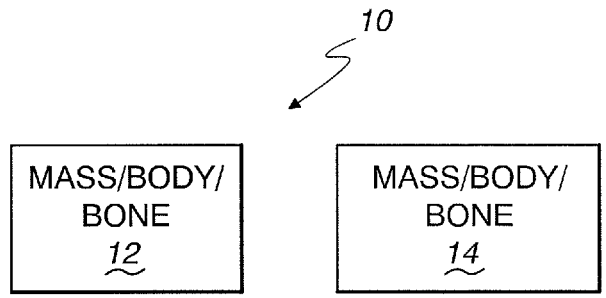
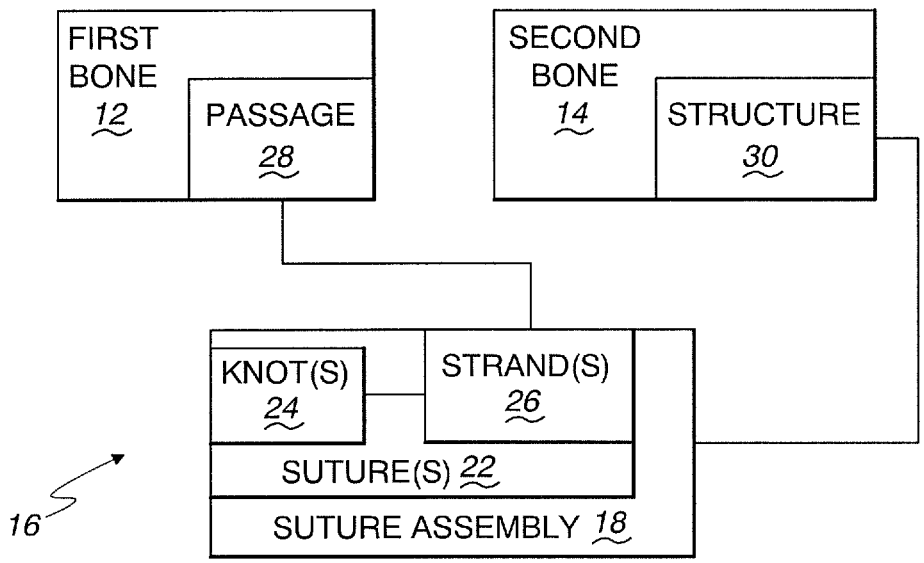
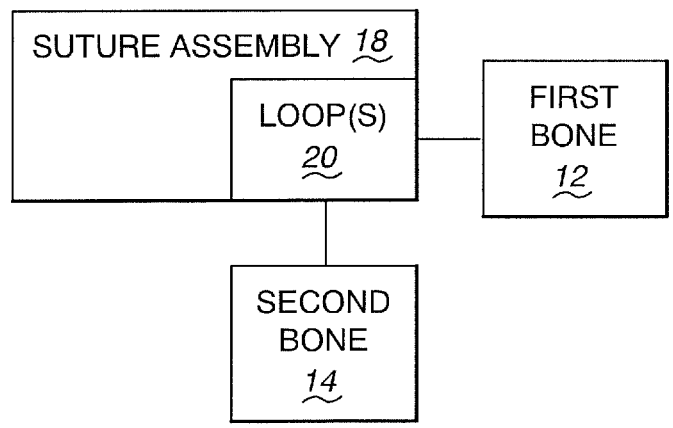

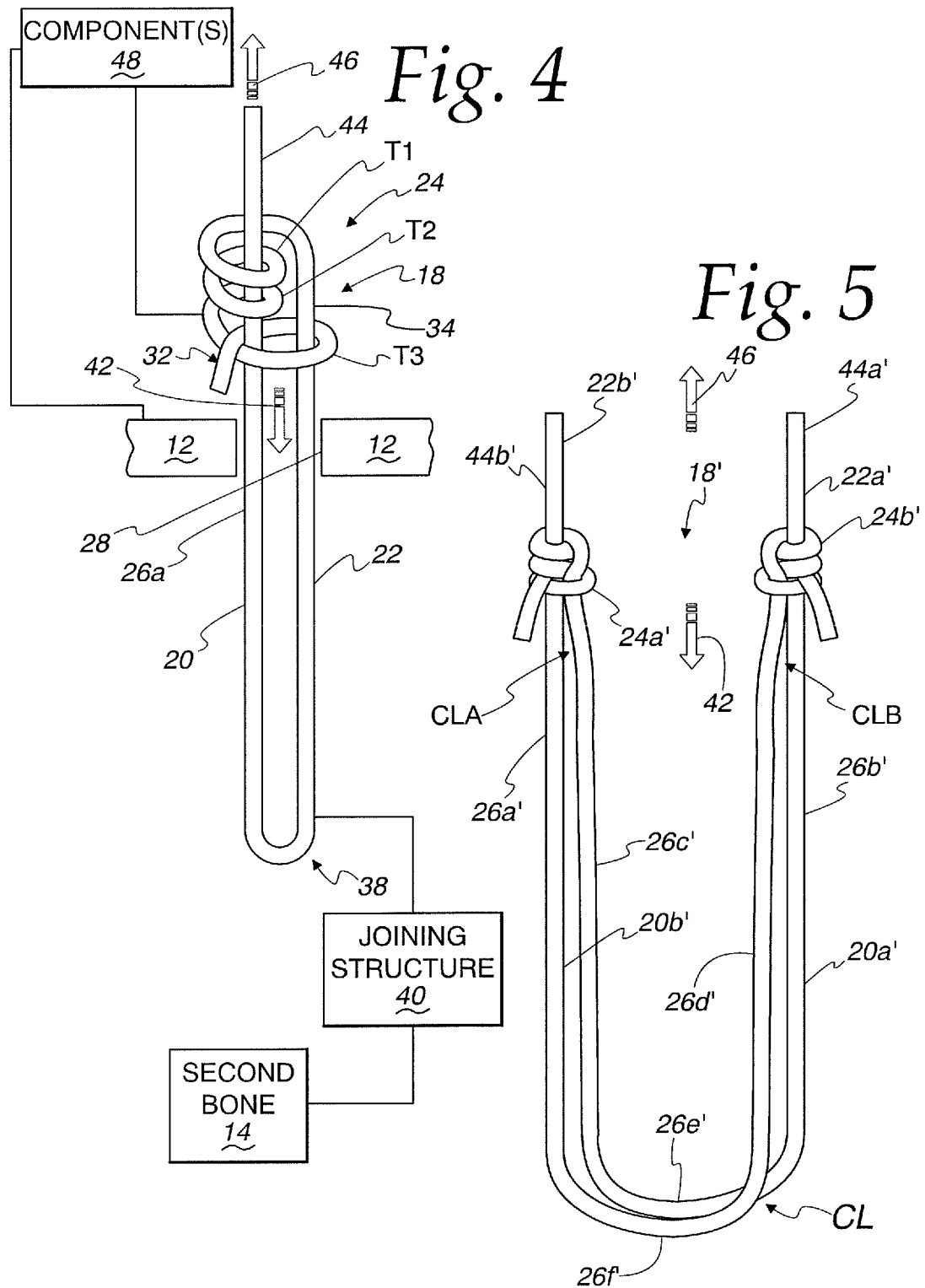

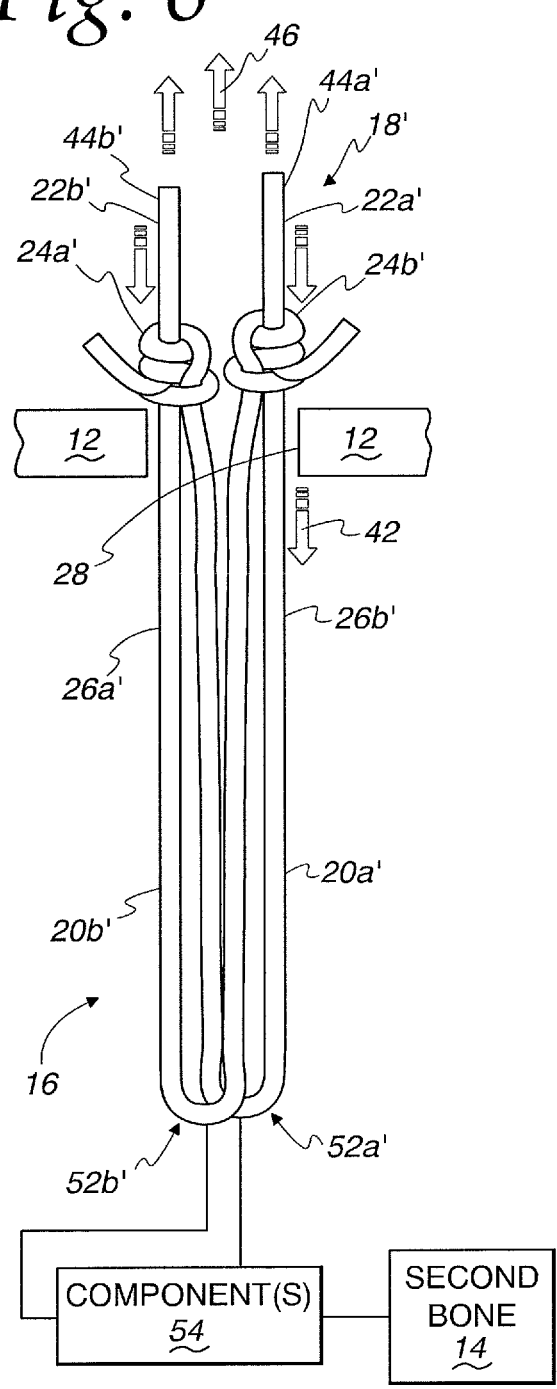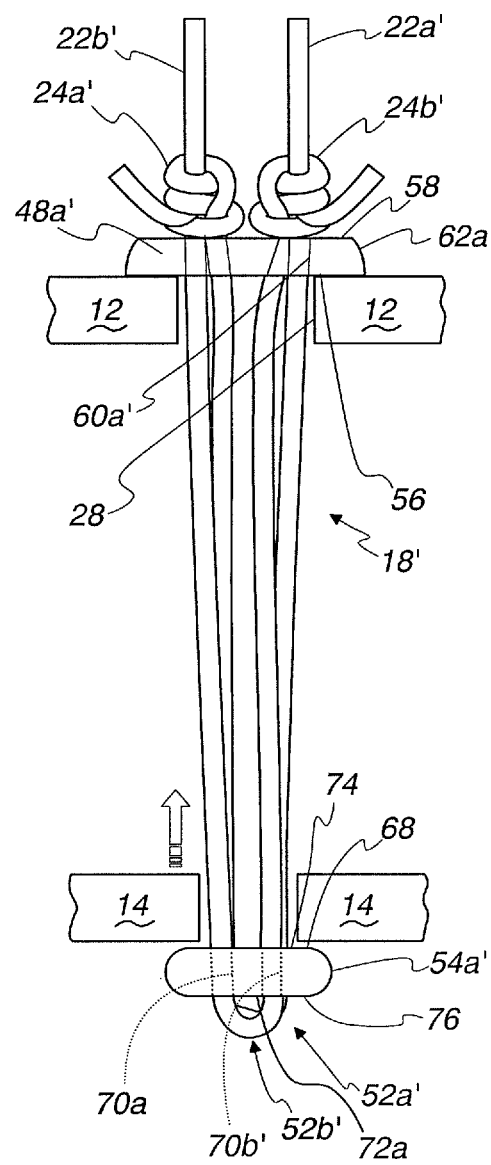

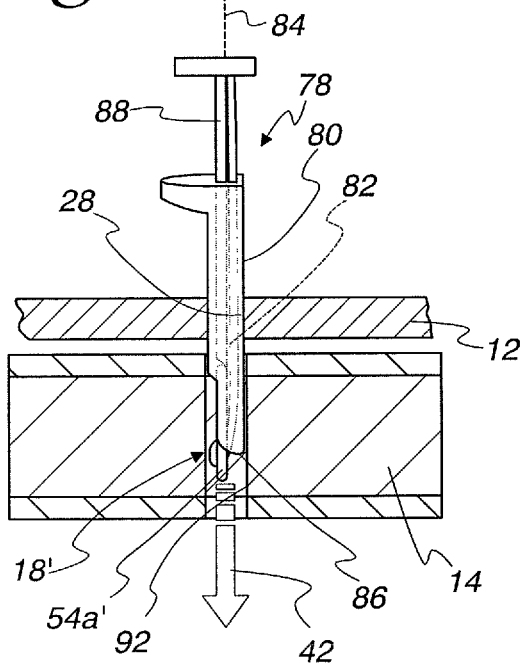
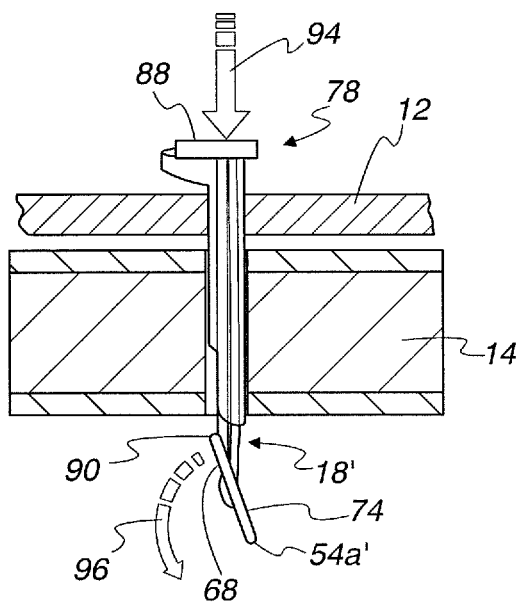
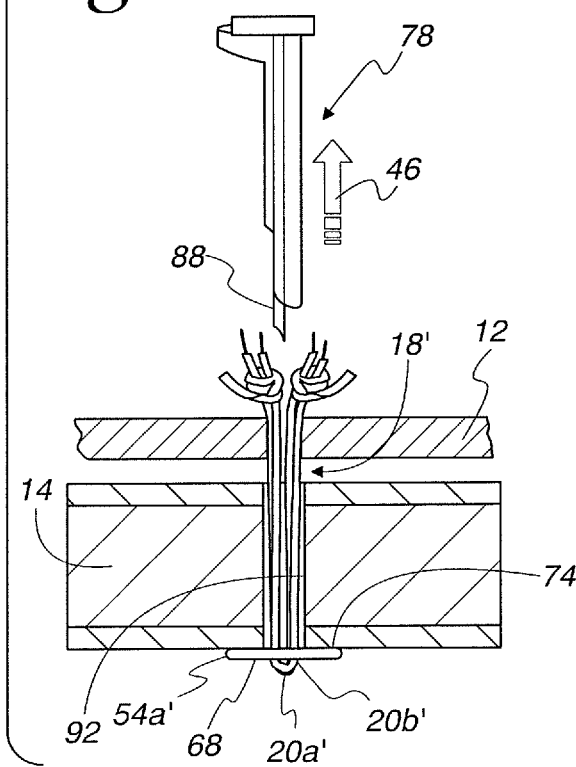

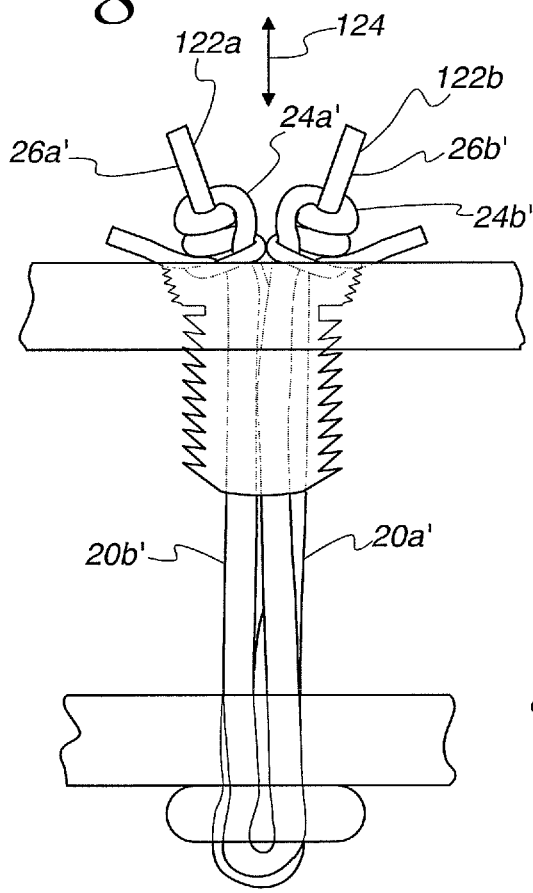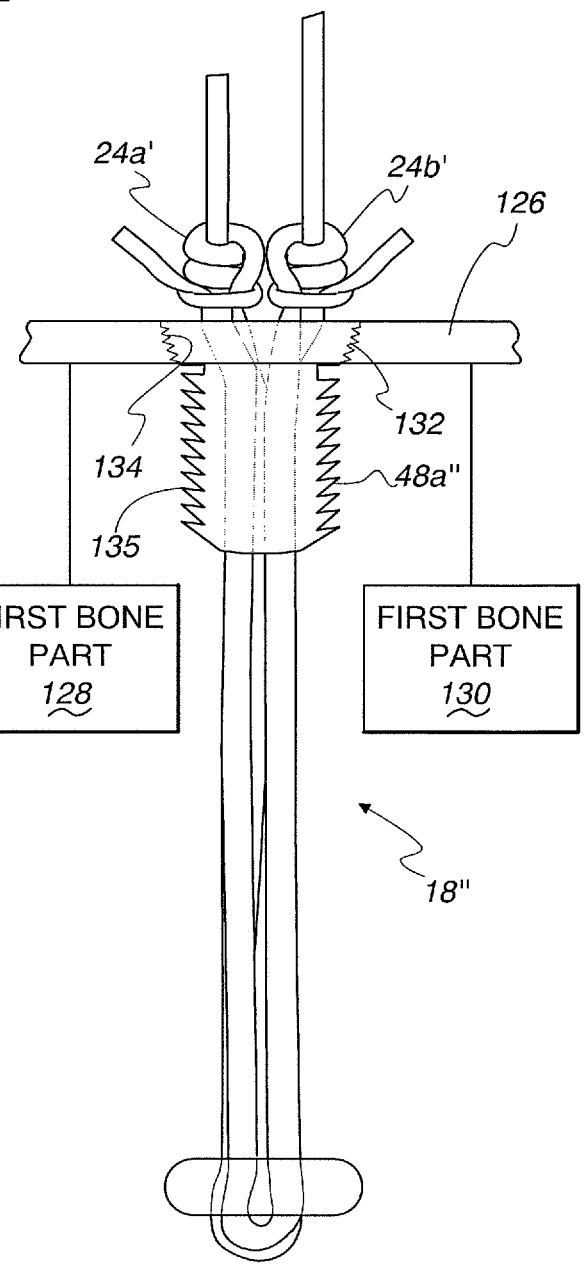

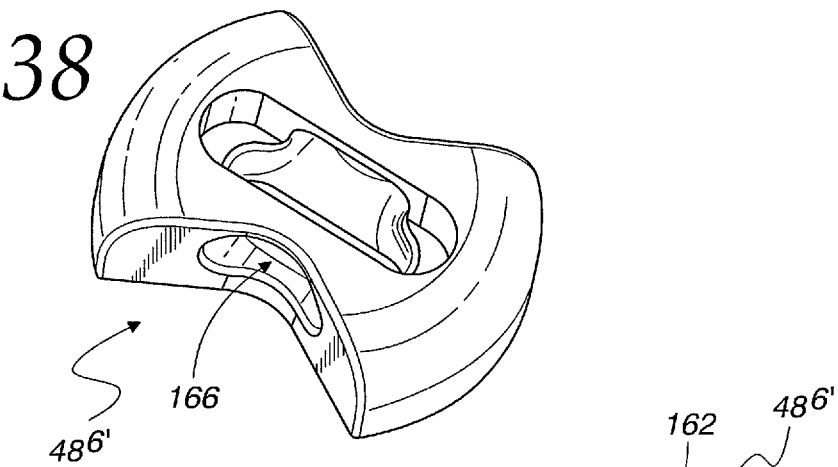
Fig. 38
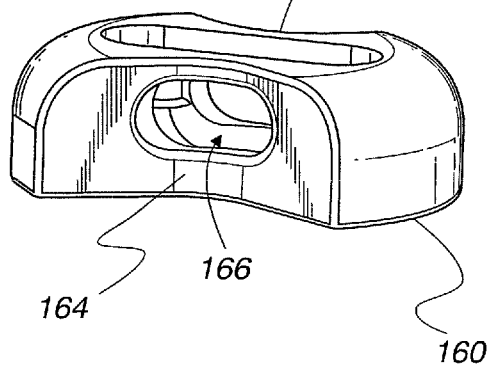
Fig. 39
Fig. 40
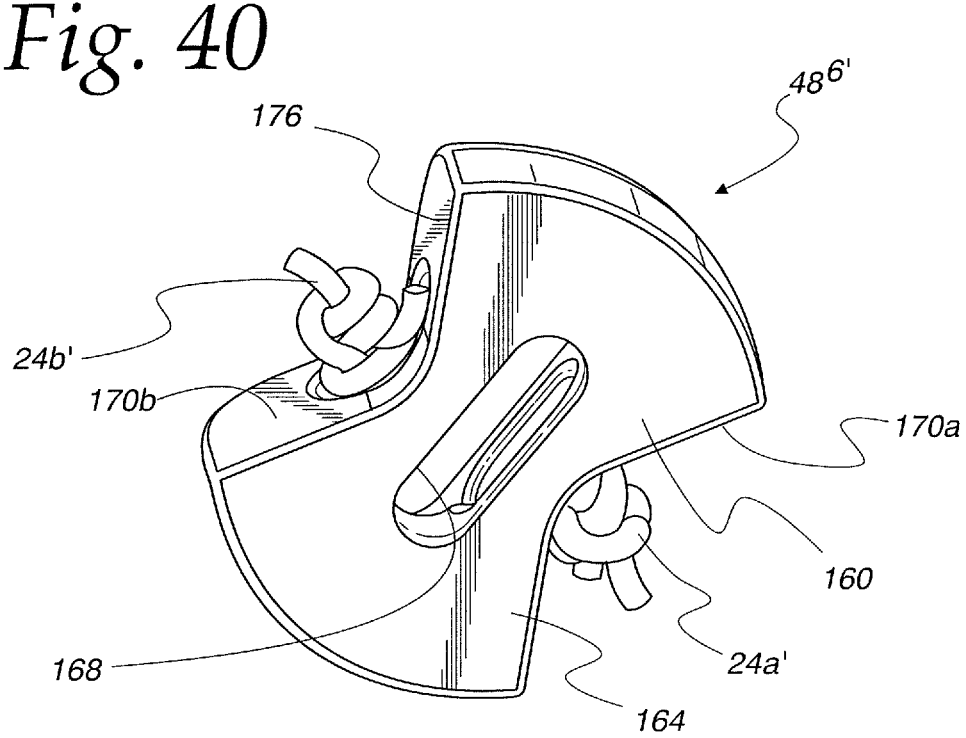

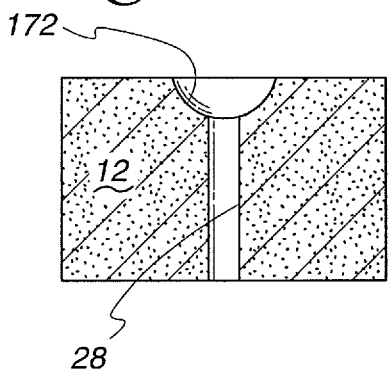
Fig. 41
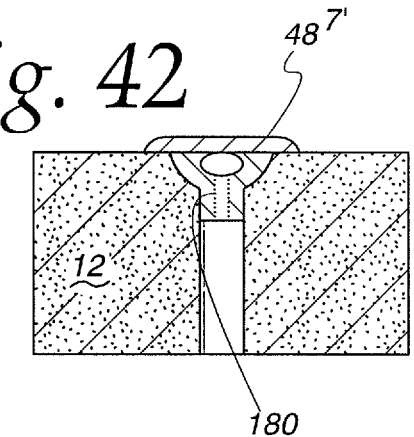
Fig. 42
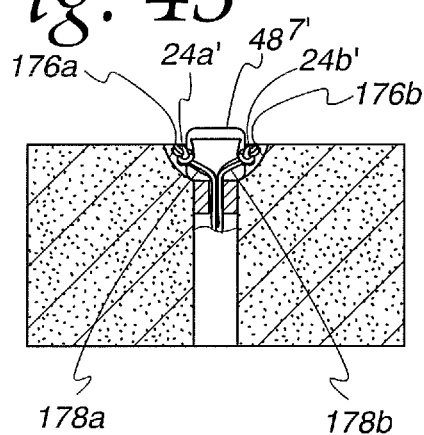
Fig. 43
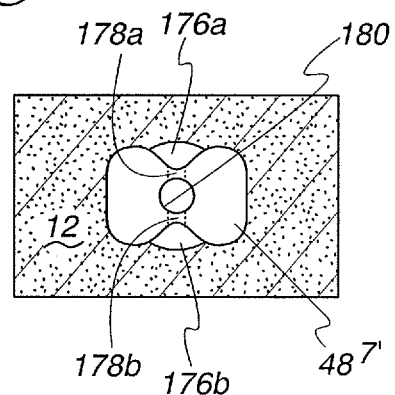
Fig. 44
Fig. 45
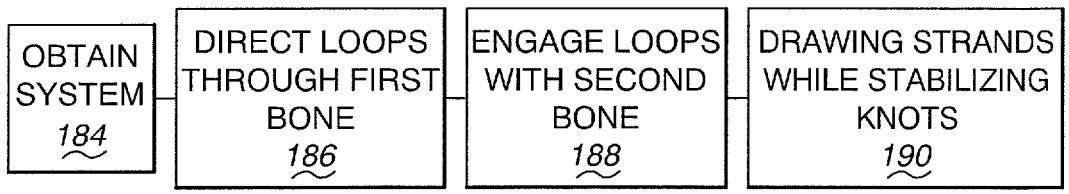

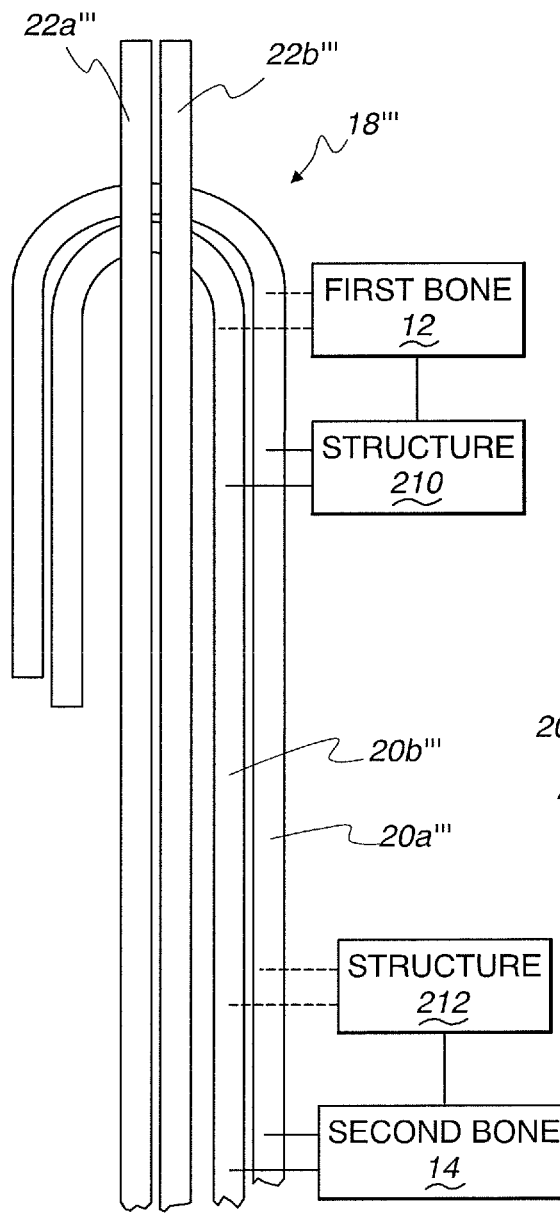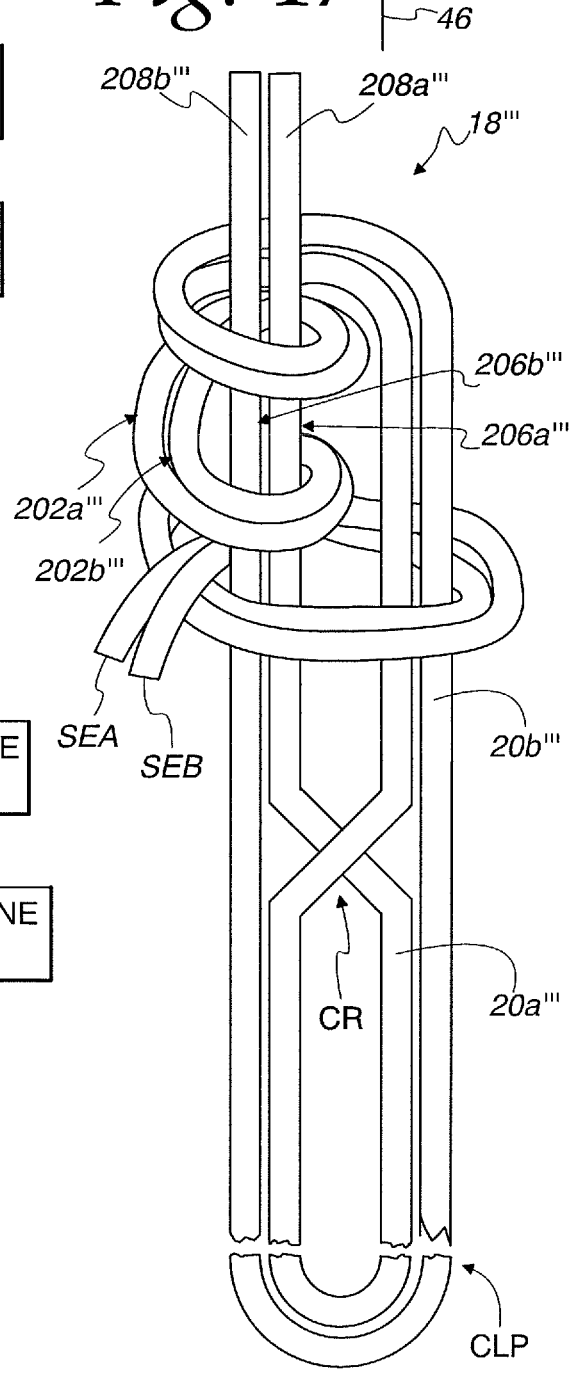

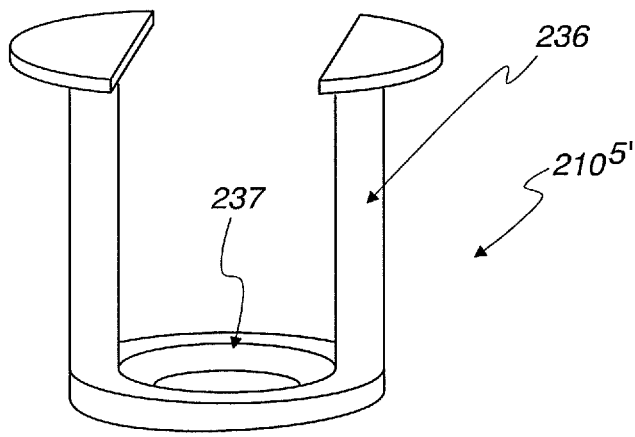
Fig. 54
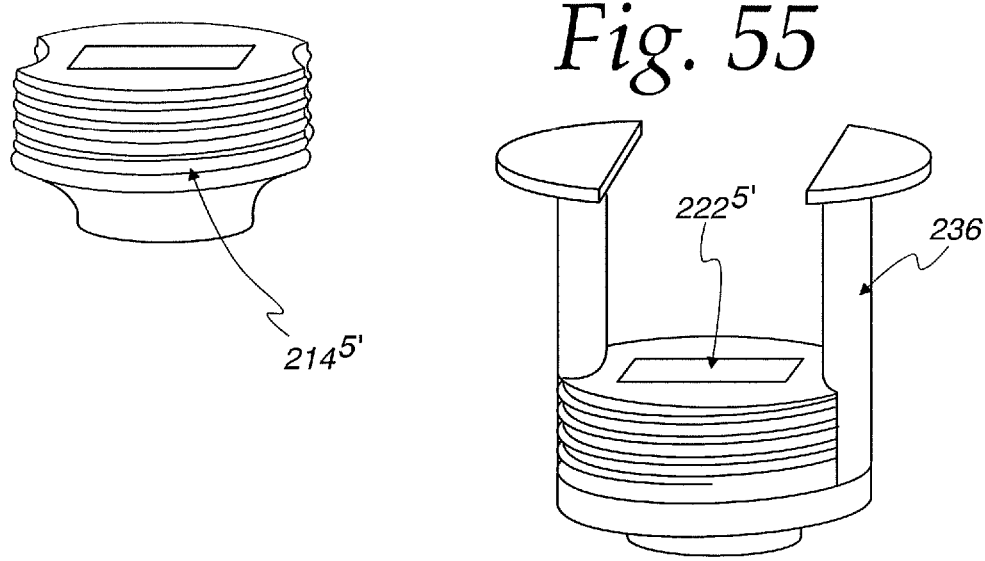
Fig. 55
Fig. 56
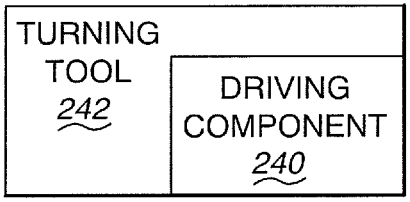 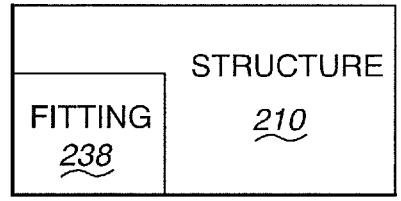

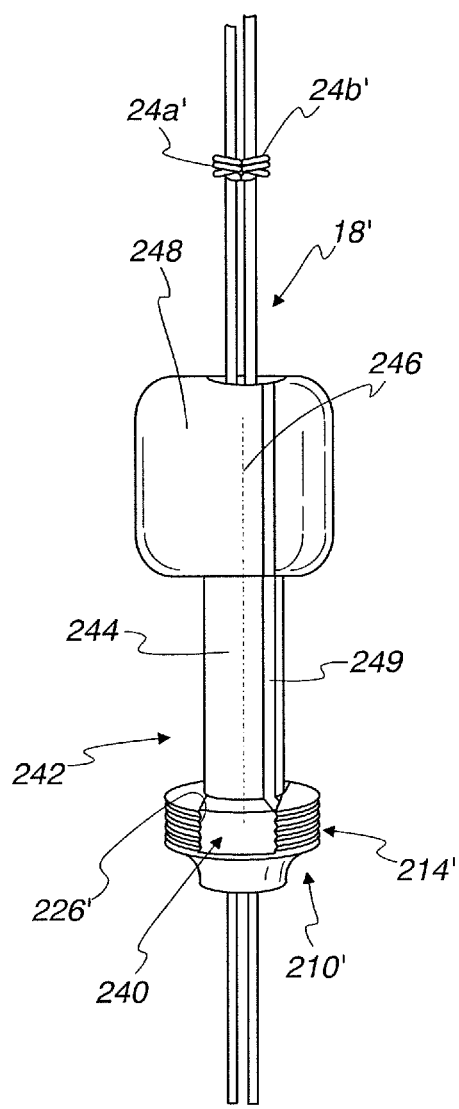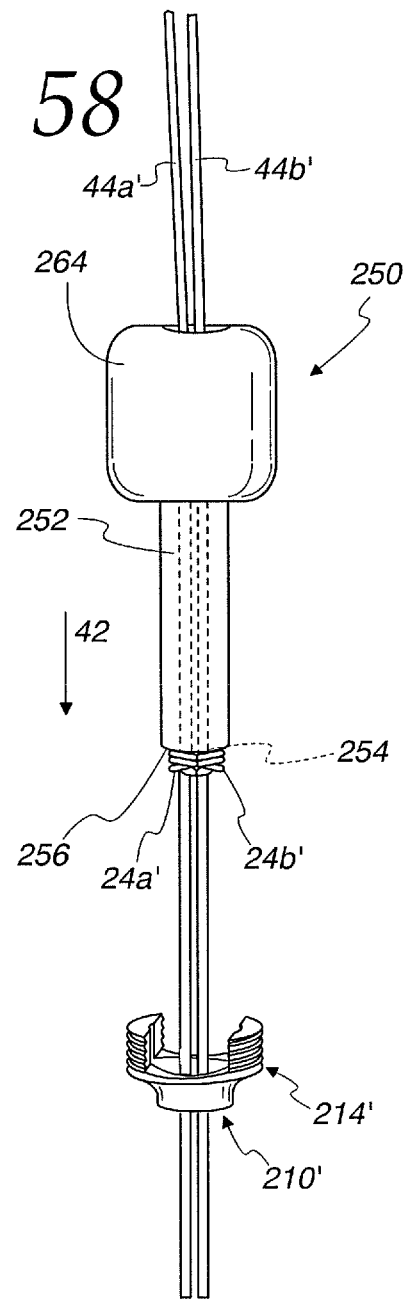

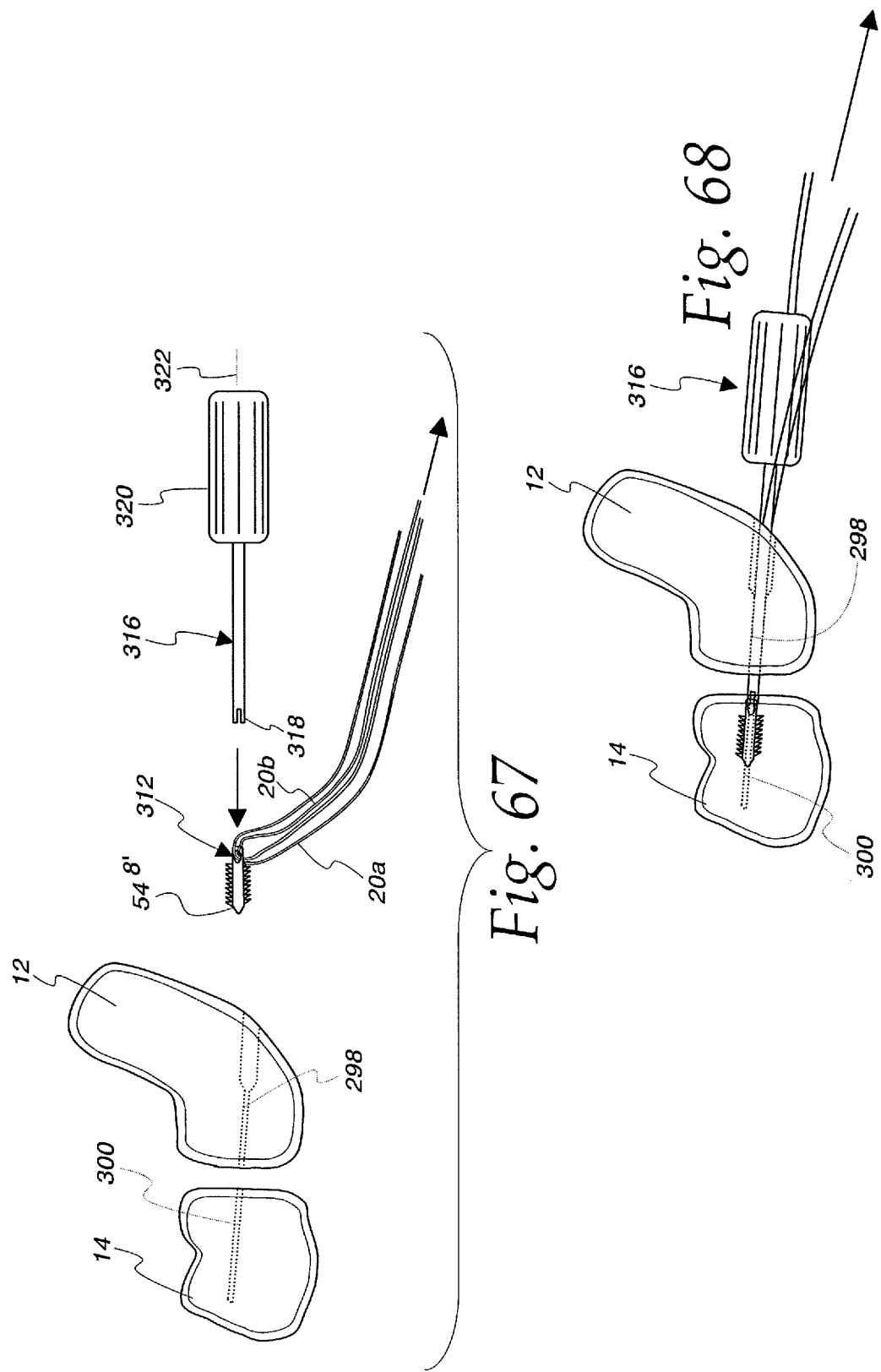

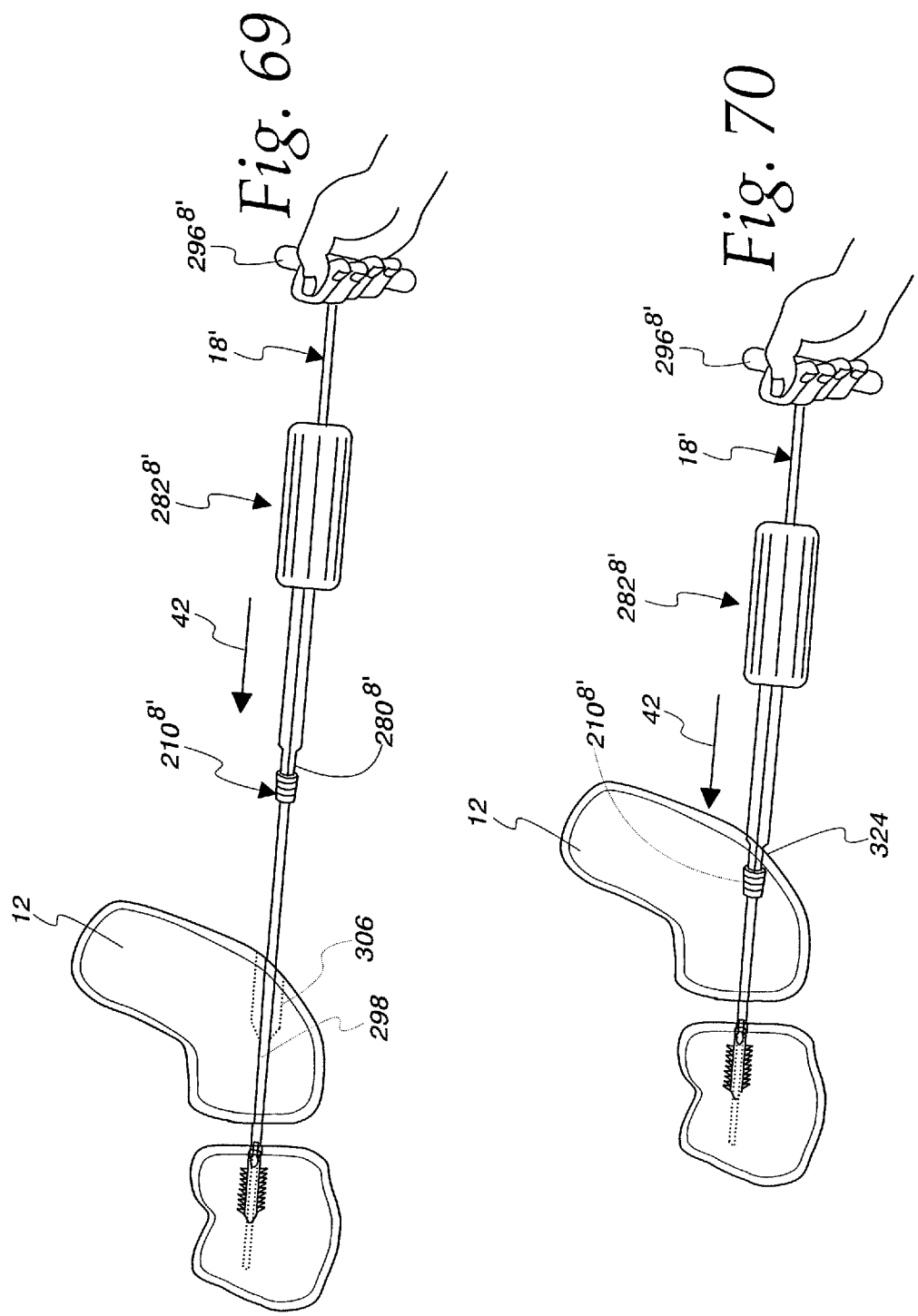

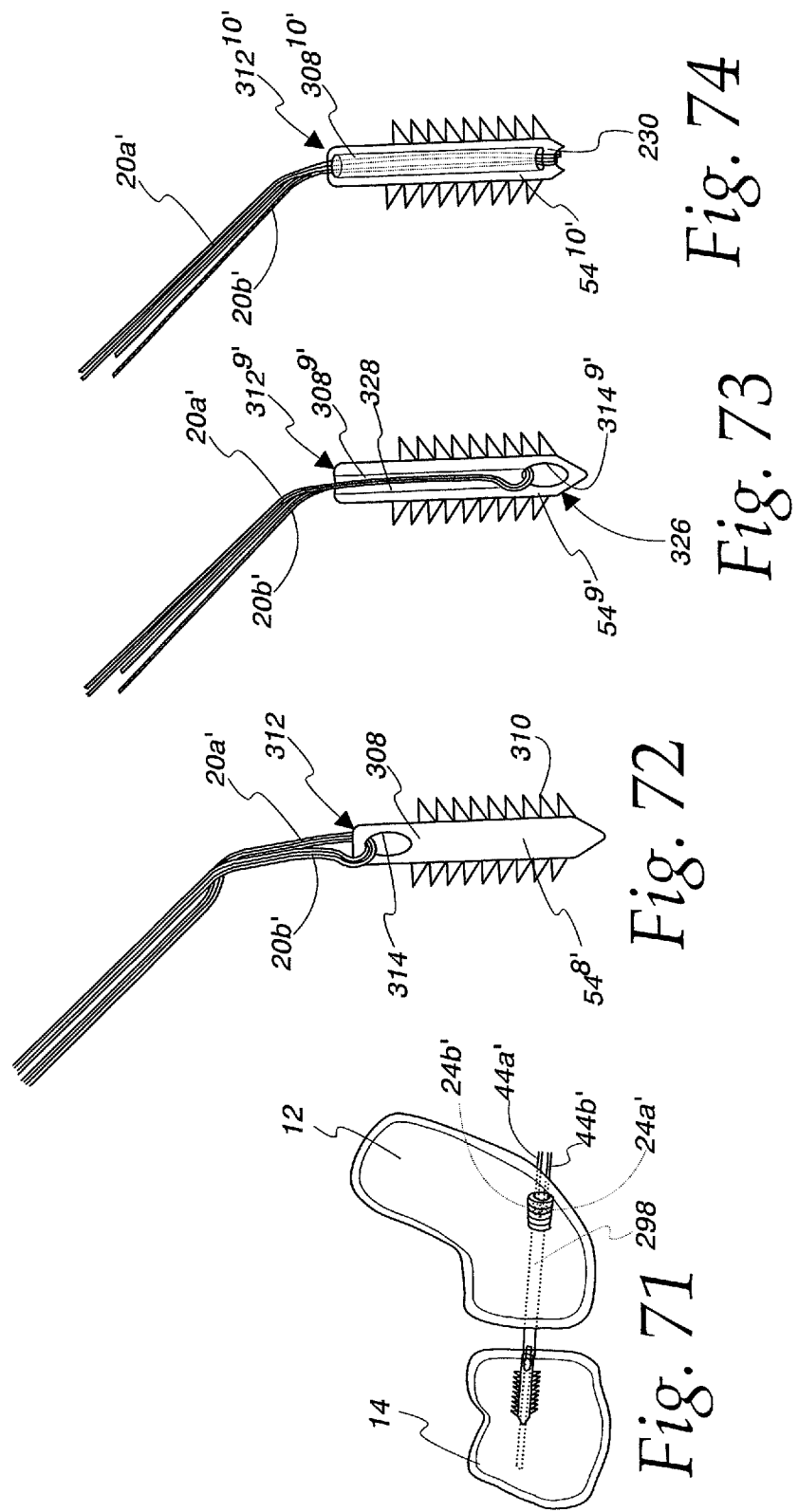

SYSTEM AND METHOD CONTROLLING A RELATIONSHIP BETWEEN FIRST AND SECOND BODIES ON A PERSON

BACKGROUND OF THE INVENTION

Field of the Invention

This invention relates to a system and method for controlling a relationship between first and second bodies on a person and, more particularly, to a system and method that utilize interosseous sutures.

Background Art

A number of medical procedures are performed that require two bodies on a person to be maintained in a predetermined relationship. These bodies may be any anatomical parts such as bones, muscles, tendons, ligaments, etc. and/or a foreign mass combined with an anatomical part or another foreign mass on or within a person. For purposes of simplicity and clarity, the description herein will focus on bodies/masses that are separate bones/bone parts.

Commonly, the bones will be spaced from each other and systems/implants are utilized to avoid separation of the bones beyond a predetermined distance. Many different systems are currently available that control a relationship between first and second bones by utilizing interosseous sutures. Typical, but not all inclusive, of applications for this type of system/implant are as follows: syndesmosis (ligament) injuries between the tibia and fibula at the ankle; correction of the first inter-metatarsal angle in bunion surgery (first/second metatarsal); acromioclavicular ligament injuries (AC separations where the clavicle is held down toward the coracoid process of the scapula); correction of scapho-lunate interosseous or other intercarpal ligament injuries; and carpometacarpal suspension of the first/second metacarpals to limit migration of the first metacarpal proximally following reconstructive surgery on the thumb carpometacarpal joint for arthritic conditions; and other ligament injuries of the musculoskeletal system.

In a common form of the interosseous suture system, described above, one or more sutures are engaged with first and second bones in a manner whereby the suture(s) can be used to draw the bones strategically towards each other to a predetermined, optimal position and then stabilized in a manner to prevent further separation. Components/anchors may be provided on one or both of the bones to anchor the sutures into bone and distribute the captive forces produced by the sutures to said bones.

The interosseous suture systems may also be broken into different categories based upon how the suture system is locked to prevent separation of the two bones. Basic categories are distinguished into knotted and knotless systems and further distinguished by how knots are formed in the sutures or the sutures are constructed and manipulated during procedures.

In one category, a surgeon is required to either fully form or complete a locked knot structure to effect final securement of an implant. Generally, it is time consuming for a surgeon to have to fully form or complete one or more knots during a procedure. Suture handling is inherently awkward. The amount of tension applied to the knot is difficult to standardize and may not be sufficient to hold the knot. Creating knots requires that two ends be drawn away from each other, preferably at a right angle to the line of the suture between the first and second bones, to avoid creation of a slip knot. This requires additional surgical exposure. There also exists the possibility that a knot may be improperly formed, which could have serious consequences that are not evident until some time after the procedure is completed.

Given the slippery nature of suture materials, and particularly synthetics, surgeons often will form multiple throws to assure that knots will not untie spontaneously. It is not uncommon for seven or more throws to be formed which consumes operative time and creates a bulk of synthetic material that often produces tissue irritation and may necessitate subsequent surgery. Formation of multiple throws also introduces a risk that one or more of the throws may not be squarely formed, resulting in a weakened holding.

While a partially-formed knot addresses the above problems to a certain extent, there remain drawbacks. A partially-formed knot typically will have a tendency to slip, thereby necessitating completion by a final cinching of the suture through additional suture manipulation. While some time may be saved using this type of system, a surgeon may be challenged to maintain the desired suture tension while the cinching is completed. The pre-formed knot structure may slip before cinching can occur, as an incident of which a less than optimal suture tension may result. This may compromise the effectiveness of the procedure and could potentially lead to a failed reconstruction.

Suture systems are also known wherein a surgeon can draw and hold two structures together with a knotless mechanism by simply applying tension to sutures to effect tightening thereof that is desirably maintained. Different mechanisms are employed to make this possible, some of which may be relatively complicated and others of which are prone to slippage. Further, some such systems have small, complicated components that are obtrusive and potentially cause ongoing irritation to a patient. Others, such as systems where one suture passes through the core of another in an arrangement like a Chinese finger trap, are difficult to deploy and use to control the amount of tension, and may be prone to slippage with cyclic loading.

While the use of knotted sutures in these procedures is highly desirable, from the standpoint of cost, ease of manipulation, and non-obtrusive post-operative construct, the industry has been continuously challenged to design better systems that afford all the above noted advantages yet are not prone to post-operative slackening or failure.

SUMMARY OF THE INVENTION

In one form, the invention is directed to a system for controlling a relationship between first and second bodies on a person. The system is made up of a suture assembly having at least a first suture configured to define, either alone or in conjunction with the first body, a restrictable loop structure with the suture assembly in an operative state. The restrictable loop structure has at least first and second restrictable sub-loops that cooperatively, either alone or in conjunction with the first body, define a first loop that can be reduced in size to thereby produce a force on the first and second bodies that urges the first and second bodies towards each other. The first and second restrictable sub-loops are respectively made up of first and second loop lengths. The first loop length has a first sliding portion with the second loop length having a second sliding portion. The suture assembly is configured to define at least one knot that extends around the first and second sliding portions. The suture assembly is configured so that the first and second sliding portions, upon each being moved within the at least one knot in a tightening sliding direction, cause a size of a respective sub-loop to be reduced. The suture assembly is further configured so that tensioning of the loop, as caused by urging the first and second bodies away from each other with the suture assembly in the operative state, causes separate first and second circumferential lengths of the first loop to be drawn away from the at least one knot. The suture assembly is configured so that drawing of each of the first and second circumferential lengths of the first loop away from the at least one knot causes the at least one knot to grasp at least one of the first and second sliding portions with a greater force that opposes enlargement of at least one of the sub-loops and thus an effective size of the first loop by resisting movement of at least one of the first and second sliding portions within the at least one knot in a direction opposite to the tightening sliding direction.

In one form, each of the first and second loop lengths defines at least part of the at least first knot.

In one form, the at least first knot consists of first and second knots. The first loop length defines one of the first and second knots. The second loop length defines the other of the first and second knots.

In one form, the suture assembly has first and second strands that with the suture assembly in the operative state are drawn away from the first body to reduce sizes of the first and second restrictable sub-loops. Lengths of the at least first suture on the first and second restrictable sub-loops move in opposite directions along a length of the first loop as the first and second strands are drawn away from the first body.

In one form, the first and second restrictable sub-loops are made up of separate first and second sutures.

In one form, the suture assembly includes first and second sutures. With the suture assembly in the operative state, the first suture is formed with a configuration that is the same as a configuration of the second suture.

In one form, the at least one knot consists of first and second knots. The suture assembly includes first and second sutures. The first and second sutures have first and second strand lengths that are maintained together and formed in the same manner to produce the first and second knots so that the first and second knots are combined to produce a double strand knot with the suture assembly in the operative state.

In one form, the at least one knot consists of first and second knots that each is one of: a) a half hitch; b) a rolling hitch; c) an adjustable bend; d) a midshipman's hitch; and e) an adjustable hitch knot.

In one form, the at least one knot consists of first and second knots. The suture assembly has at least one component that resides between each of the first and second knots and the first body with the suture assembly in the operative state. The at least one component is configured to block advancing of the first and second knots through the at least one component.

In one form, with the suture assembly in the operative state, the first and second restrictable sub-loops extend each through the other.

In one form, with the suture assembly in the operative state, the restrictable loop structure extends around at least one of: a) the second body; b) a structure on the second body configured so that the restrictable loop structure limits movement of the first and second bodies away from each other.

In one form, the first and second bodies are first and second bones.

In one form, the first loop extends around structure on the second bone with the suture assembly in the operative state. The structure on the second bone is configured to define a second loop. The first loop and second loop extend each through the other with the system in the operative state. The first loop and second loop cooperate to limit movement of the first and second bones away from each other.

In one form, the at least one knot consists of first and second knots. The system is provided in combination with a knot pusher that is configured to engage and stabilize at least one of the first and second knots as the first and second strands are drawn away from the first body to thereby reduce sizes of the first and second restrictable sub-loops.

In one form, the suture assembly further includes at least one component that resides between portions of the restrictable sub-loops and the second body.

In one form, the at least one knot consists of first and second knots. The suture assembly has at least one component configured to abut to the first bone. The at least one component defines a surface that abuts to each of the first and second knots with the suture assembly in the operative state to thereby block advancing of the first and second knots through the at least one component.

In one form, the at least one component defines a receptacle configured to receive at least a portion of at least one of the first and second knots.

In one form, the at least one knot consists of first and second knots. The system further includes a plate configured to be fixed to the first bone to stabilize parts of the first bone near a fracture. The suture assembly further includes a component that is configured to be fixed to the plate and define a surface that abuts to at least one of the first and second knots with the suture assembly in the operative state to thereby block advancing of the first and second knots through the first bone.

In one form, the component is configured to be anchored within the first bone with the suture assembly in the operative state.

In one form, the second loop is defined by at least one component that is configured to be anchored in the second bone.

In one form, the second loop is defined by at least one component that is configured to be anchored on the second bone.

In one form, the first and second bodies are first and second bones. The at least one component has a body with an elongate shape to facilitate advancement through openings in the first and second bones.

In one form, the system is provided in combination with an introduction assembly that is configured to advance the first and second restrictabie sub-loops through at least one of the first and second bones.

In one form, the at least one component defines a receptacle to receive a majority of the first and second knots.

In one form, the at least one component is threaded to engage one of: a) the first bone; and b) a plate connected to the first bone.

In one form, the at least one component has a fitting to accommodate a turning tool.

In one form, the system is provided in combination with a turning tool with a driving component configured to make a keyed connection with the fitting on the at least one component.

In one form, the turning tool further includes an elongate sleeve with a lengthwise axis.

In one form, the at least one knot consists of first and second knots. Tension applied to the first and second circumferential lengths in a direction away from each of the first and second knots causes each of the first and second knots to reconfigure a respective length of the at least first suture that it extends around to assume a non-linear shape through the knot resulting in increased resistance to sliding.

In one form, the at least one component defines a receptacle to receive substantially an entirety of the first and second knots.

In one form, the invention is directed to a method of controlling a relationship between first and second bodies each in the form of a bone on a person. The method includes the steps of: obtaining a system as described above; with the suture assembly in a starting state, directing portions of the first and second restrictable sub-loops through at least one passage in the first bone; engaging the first and second sub-loops either directly or indirectly with the second bone; and, with the first and second sub-loops engaged with the second bone, simultaneously drawing parts of the at least first suture away from the first bone while stabilizing the at least one knot to thereby produce a tension on the first and second restrictable sub-loops selected to maintain a desired relationship between the first and second bones.

In one form, the system further includes at least one component that resides between the at least one knot and the first bone with the suture assembly in the operative state. The at least one component is configured to block advancing of the at least one knot through the at least one passage. The step of drawing parts of the at least first suture while stabilizing the at least one knot includes causing the at least one knot to bear against the at least one component.

In one form, the at least one component has a receptacle. The step of drawing parts of the at least first suture while stabilizing the at least one knot includes causing at least part of the at least one knot to reside in the receptacle as the parts of the at least first suture are being drawn to reduce the sizes of the first and second restrictable sub-loops.

In one form, the at least one component has a receptacle. The step of drawing parts of the at least first suture while stabilizing the at least one knot includes causing substantially an entirety of the at least one knot to reside in the receptacle as the parts of the at least first suture are being drawn.

In one form, the method further includes the step of recessing the at least one component in the first bone.

In one form, the at least one knot is configured so that the at least one knot is blocked from moving through the at least one passage in the first bone.

BRIEF DESCRIPTION OF THE DRAWINGS

FIG. 1 is a schematic representation of an environment in which the present invention can be utilized;

FIG. 2 is a schematic representation of a system for controlling a relationship between first and second bones, according to the present invention;

FIG. 3 is a schematic representation showing additional details of a suture assembly, on the system in FIG. 2, that cooperates between first and second bones;

FIG. 4 is a partially schematic depiction of one form of suture assembly, according to the present invention, in an operative and starting state, and engaged with first and second bones and with a knot on the suture assembly pre-formed but uncinched;

FIG. 5 is a view as in FIG. 4 of a modified form of suture assembly in an operative and starting state;

FIG. 6 is a partially schematic representation of the inventive system in FIG. 5 with the suture assembly in an operative and secured state with respect to first and second bones;

FIG. 7 is a view as in FIG. 6 wherein a component is provided between two knots and a first bone and with a specific form of component, as shown schematically in FIG. 6, that cooperates with the second bone;

FIGS. 18-20 show sequentially the insertion of the inventive suture assembly through first and second bones using an introduction assembly;

FIG. 26 is a view as in FIG. 25 showing a modified form of component that causes standing ends of the sutures extending through knots to be bent;

FIG. 27 is a view as in FIG. 24 wherein the component cooperates with a plate that is used to stabilize bone parts in the vicinity of a fracture;

FIG. 38 is an enlarged, perspective view of a still further modified form of component acting between the knots and first bone;

FIG. 39 is a view of the component in FIG. 38 from a different perspective;

FIG. 40 is a view of the component in FIGS. 38 and 39 from a still further different perspective and showing the relationship to the sutures;

FIG. 41 is a cross-sectional view of the first bone with a passage modified with a counterbore to receive another form of component acting between the first bone and knots on the inventive suture assembly;

FIG. 42 is a view as in FIG. 41 with the component inserted;

FIG. 43 is a view as in FIG. 42 with the component turned through approximately 90° within the first bone passage;

FIG. 44 is an end view of the component on the first bone;

FIG. 45 is a schematic representation of a method for controlling a relationship between first and second bones, according to the present invention;

FIG. 46 is a partially schematic depiction of another form of suture assembly, according to the present invention, in a starting state;

FIG. 47 is a view as in FIG. 46 wherein the suture assembly is in an operative state and a double strand knot on the suture assembly is pre-formed but uncinched;

FIG. 54 is an exploded, perspective view of yet another form of the inventive blocking structure;

FIG. 55 is a view as in FIG. 54 with the parts assembled;

FIG. 56 is a schematic representation of a turning tool for certain of the inventive blocking structures;

FIG. 57 is a perspective view of the blocking structure in FIG. 50 engaged with one form of turning tool, as shown schematically in FIG. 56 and associated with first and second sutures, formed with two knots, as in FIG. 5, with the suture assembly in an operative state;

FIG. 58 is a view as in FIG. 57 with the turning tool removed and a knot pushing assembly operatively positioned;

FIGS. 65-71 are partially schematic representations sequentially showing a method of using the inventive structure to control the relationship between lunate and scaphoid bones;

FIGS. 72-74 are enlarged elevation views of alternative form of components that are anchored in the lunate bone to carry out the procedure in FIGS. 65-71.

DETAILED DESCRIPTION OF THE PREFERRED EMBODIMENT

Figure 8:
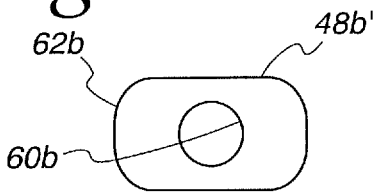
FIG. 8 is an end view of one form of component that cooperates between the knots and first bone as shown in FIG. 7.

In FIG. 1, a generic environment for the present invention is shown at 10. The invention is designed for anatomical repair/reconstruction and interacts between a first mass/body/bone 12 and a second mass/body/bone 14. At least one of the masses/bodies 12, 14 might be a ligament, muscle, or other soft tissue. The masses/bodies 12, 14 may both be soft tissue. Alternatively, the masses/bodies/bones 12, 14 may be a combination of soft tissue and bone. Still further, one of the masses/bodies 12, 14 may be a foreign body integrated into the human anatomy. As but one example, a vessel may be tied around a vascular stent. Both of the masses/bodies 12, 14 could be foreign bodies, such as implants integrated into a person's anatomy. For purposes of simplicity, as used hereinbelow in the description and claims, "body" generically encompasses the aforementioned "masses" and "bones".

While described herein in relationship to a "person", the inventive concepts can be used on non-human subjects. For purposes of simplicity and clarity, the invention will be described herein as used with first and second bones on a human. However, while useful in describing the operation of the invention, this application should not be viewed as limiting.

The invention is particularly useful in cooperating between first and second bones 12, 14 that are required to be drawn against each other or first and second bones 12, 14 that, as part of a procedure, are required to be urged towards each other in order to limit the separation between the two bones below a specific value but otherwise to allow continued relative movement between the bones within this limit of separation.

As shown in FIG. 2, the invention is directed to a system, or implant, at 16 for controlling a relationship between the first and second bones 12, 14. The system 16 includes a suture assembly 18 that is configured to be placed in an operative state wherein the suture assembly defines at least one restrictable loop 20, as shown schematically in FIG. 3, that cooperates between the first and second bones 12, 14. In different forms herein, a loop 20 may be a continuous shape formed by the suture assembly 18. Alternatively, the continuous shape of the loop 20 may be formed partially by the first bone 12 and/or second bone 14 in conjunction with the suture assembly 18. For purposes of simplicity, the suture assembly 18 is considered to be forming the loop, even if a portion thereof is defined by the first bone 12 and/or second bone 14.

The suture assembly 18 is made up of at least one suture 22. "Suture", as used herein, is intended to encompass a standard suture construction, and all other constructions, such as stainless steel cable, suture tape, cord, etc., that can perform the same basic function of a standard suture. At least one knot 24 is formed in one of the sutures 22. With the suture assembly 18 in its operative state, the knot 24 extends around a length of a strand 26 that is directed through a passage 28, with a strategically selected size, in the first bone 12. By stabilizing the knot 24 and drawing the same or another strand 26 away from the first bone 12, the strand slides through the knot 24 and the size of the loop 20 is reduced. As the loop 20 restricts in size, the stabilized knot 24 shifts in a first direction, toward the first bone 12.

The suture assembly 18 is configured so that: a) with the suture assembly 18 in the operative state and the restrictable loop 20 placed under a first tension, the knot 24 grasps the strand 26 where the knot 24 surrounds the strand 26 with a first force that maintains the size of the restrictable loop 20; and b) with the suture assembly 18 in the operative state and the loop 20 placed under a tension greater than the first tension, the knot 24 grasps the strand 26 where the knot 24 surrounds the strand 26 with a force greater than the first force that maintains the size of the restrictable loop 20.

With the suture assembly 18 in its operative state and secured, the knot 24 is blocked from advancing through the passage 28.

With the suture assembly 18 in its operative state, the loop 20 extends around at least one of: a) the second bone 14; and b) structure 30 on or associated with the second bone 14 configured so that the loop 20 limits movement of the first and second bones 12, 14 away from each other and can be restricted to draw the first and second bones 12, 14 towards, and potentially against, each other.

Specific forms of the system 16 will now be described. It should be understood that the exemplary forms are not intended to be limiting, as the generic showing of components in FIGS. 2 and 3 is intended to encompass the specific components herein described, as well as virtually an unlimited number of variations thereof and their interactions.

In one basic form, as shown in FIG. 4, the suture assembly 18 consists of a single suture 22 that forms a self-contained loop 20. The knot 24 depicted is an adjustable bend knot wherein a free end of the knotted portion of the suture part 32 is directed around the strand 26a to produce two full turns T1, T2 around the strand 26a. Although the drawing shows two full turns, the number of turns could be different to select a desired resistance to sliding of the strand 26a. The free end part 32 is then wrapped around a parallel strand 34 and the strand 26a to produce a separate turn T3 with the free end part 32 thereafter projected between the turns T2, T3. For purposes of simplicity in describing this and other embodiments, the separate parallel lengths of the suture 22 are considered separate "strands", even though they are part of the same suture 22. By stabilizing the knot 24 and drawing the part 32, the knot 24 grasps a length of the strand 26a around which it extends. The suture assembly 18 is thereby in a preformed operative and starting state.

The loop 20 can then be directed through the passage 28 through the first bone 12 such that the distal loop end 38 is moved in the vicinity of the second bone 14 to be joined thereto by appropriate joining structure at 40. The joining structure 40 may take a number of different forms including, but not limited to, those described hereinbelow for different embodiments. It suffices to say at this stage that the joining structure 40 allows the loop 20 to restrict in size with the knot 24 blocked from being moved through the passage 28 in the first direction as indicated by the arrow 42, as an incident of which a force is applied to the second bone 14, urging it in the first direction towards the first bone 12. This restriction is effected by drawing a part 44 of the strand 34 in a direction opposite to the first direction, as indicated by the arrow 46, while stabilizing the completed knot 24 which resultingly moves in the first direction toward the first bone 12. The drawing direction for the strand 34 is substantially parallel to a line of force applied between the first and second bones 12, 14.

With knot 24 blocked from movement, tension on the strand 44 in the first direction causes the suture to narrow under load as well as tend towards a straight linear path through the knot 24, causing the strand 26a to slide in the first direction to reduce the size of the loop 20. On the other hand, with tension applied to the loop oppositely to the first direction, tightening of the knot 24 around the strand 26a causes the knot 24 to locally bend the path of the strand 26a around material in the knot 24 over a non-linear path as well as grasp the strand 26a around its circumference, resulting in locking of the strand 26a within the knot 24 and preventing enlargement of the loop 20.

The showing in FIG. 4 is somewhat schematic in nature. It is contemplated that with the knot 24 tightened from its FIG. 4 configuration, it might have a suitable effective size that it will be blocked from moving into and through the passage 28.

Alternatively, one or more components 48 may be interposed between the knot 24 and first bone 12 to block advancement of the knot 24 through the passage 28.

The adjustable bend knot 24 is formed so that the loop 20 can be tensioned whereby the knot 24 positively grasps the strand 26a and prevents sliding of the knot 24 under forces imparted by the first and second bones 12, 14, tending to move away from each other. Further, the adjustable bend knot 24 is configured so that movement of the bones 12, 14 away from each other causes a tension on the loop 20 that enhances the integrity of the implant 18 by increasing the grasping force of the knot 24 on the strand 26a, thereby to more positively maintain the optimally selected size of the loop 20.

Maintenance of the set loop size is further assisted by the interaction of the loop 20 with the second bone 14 and/or the joining structure as well as the non-linear path through knot 24 to dissipate the load through a capstan effect.

Accordingly, the surgeon is required only to obtain the suture assembly 18 with the preformed knot 24, direct the loop 20 through the passage 28 to engage the second bone 14, and draw the first strand part 44 in the second direction while stabilizing the knot 24, as an incident of which the knot 24 advances in the first direction. The knot 24 will become cinched against the resistant pressure generated by the bones 12, 14, which are either against each other or normally urged away from each other by the patient's musculoskeletal system. The surgeon is not required to create any further knots, though it is conceivable that additional knots may be made to further enhance the integrity and holding ability of the knot 24. The surgeon need only remove the excess of the drawn strand part 44 and the suture part 32.

While the adjustable bend configuration is described for the knot 24, it is contemplated that other knot configurations are usable as well. Within the generic showing, the knot 24 in FIG. 2 is intended to encompass, for example, a half hitch knot, a rolling hitch knot, a midshipman's hitch knot, an adjustable hitch knot, and any other knot that will cinch in the system 16 as described herein. Essentially, the contemplated knots are grasping knots that will cinch further, and thus become more secure when an associated loop is further tensioned, which in the system 16 occurs as the bones 12, 14 are urged away from each other with the suture assembly 18 in its operative state. The knot 24 defines a stopper knot that will not advance through the passage 28 and will brace against the first bone 12, directly or indirectly, to allow effective further tightening of the knot 24 as the initial procedure is carried out by the surgeon to fix the system 16.

It should be noted that throughout the description herein, and the claims, the drawing of the strand parts and resulting shifting of the knot along a length of a strand that it surrounds, while described to occur in first and second opposite directions, may not occur in perfectly parallel paths. "First and second directions" as used herein are intended to be general in nature, but are clear enough to understand how relative movement occurs between the various suture assembly parts as the system 16 is utilized.

A more preferred form of suture assembly is shown in FIGS. 5-44 at 18'. The suture assembly 18' utilizes first and second sutures 22a'. 22b' which cooperate to produce part or all of a first loop 20a' and second loop 20b'. A first knot 24a' is formed by the first suture 22a', with a second knot 24b' formed by the second suture 22b'. The knot 24a' surrounds a first strand 26a' on the second suture 22b', with the second knot 24b' surrounding a second strand 26b' on the first suture 22a'. The first suture has a free part/end 44a' that is part of the second strand 26b'. The second suture 22b' has a free part/end 44b' that is part of the first strand 26a'. The strand parts 44a', 44b' are drawn in the aforementioned second direction, as indicated by the arrow 46, to reduce the size of the first and second loops 20a', 20a'.

With the suture assembly 18' in FIG. 5, the first and second loops 20a', 20b', as the various other forms of loop 20 herein, define restrictable "sub-loops" that together make up a restrictable loop structure and define a combined loop CL that can be reduced in size to thereby produce a force on the mass/body/bone 12 and mass/body/bone 14 that urges them towards and/or against each other. Drawing the free ends 44a', 44b' in the first direction causes tensioning of the suture loops 20a', 20b' in opposite directions along the length of the combined loop CL. As a result, when tension is applied on separate circumferential lengths CLA, CLB of the combined loop CL in a direction away from the knots 24a', 24b', each of the first knots 24a', 24b' will: a) grasp a respective length of suture that it extends around with a greater force; and b) reconfigure a respective length of suture that it extends around into a non-linear shape through the knot 24a', 24b' to thereby resist sliding movement of the suture lengths in the knots 24a', 24b'. By resistance enlargement of one of the suture loops 20a', 20b' by drawing either of loop lengths CLA, CLB, the effective size of the combined loop CL is effectively maintained.

With the suture assembly 18' in the initial operative and starting state of FIG. 5, the suture assembly 18' can be shaped as in FIG. 6 to advance the loops 20a', 20b' through the passage 28 in the first bone 12.

Distal loop portions 52a', 52b' interact with the second bone 14 in a manner that by reducing the size of the loops 20a', 20b', with the knots 24a', 24b' braced relative to the first bone 12, the first and second bones 12, 14 are drawn towards each other. The precise manner for connecting the loop portions 52a', 52b' with the second bone 14 is not critical to the present invention. For purposes of initial discussion, at least one component 54 is shown to interconnect the loop portions 52a', 52b' with the second bone 14. The component(s) 54 may be configured so that the loops 20a', 20b' cooperatively extend around part of the second bone. Alternatively, the component(s) 54 can function as an anchor at the second bone 14.

The component(s) 54 may be configured so that the loops 20a', 20b' are independently connected to the second bone 14. More preferably, the component(s) 54 are configured so that the loops 20a', 20b' function together as a combined loop with, in this embodiment, two pairs of loop-forming strands.

With the system 16 in the FIG. 6 configuration, as the size of the loops 20a', 20b' is reduced, the first and second knots 24a', 24b' shift in the first direction, indicated by the arrow 42, along a length of their respective strand 26a', 26b' that is directed through the passage 28. This occurs as a result of the parts 44a', 44b' of the strands 26b', 26a', respectively, being drawn away from the first bone 12 in the second direction, as indicated by the arrow 46, with the knots 24a', 24b' stabilized, to thereby reduce the size of each of the loops 20a', 20b'. In other words, sliding portions move in a tightening sliding direction within a respective knot 24a', 24b' to cause a respective loop 20a', 20b' to reduce in size.

As depicted, in a somewhat schematic sense in FIG. 6, the knots 24a', 24b' can be abutted directly to the bone 12 around the passage 28 so that they cooperatively produce a mass that cannot be advanced into/through the passage 28. The knots 24a', 24b' thereby become braced so as to allow an appropriate tension to be applied to the drawn suture parts 44a', 44b' to cinch the knots 24a', 24b'. This tension is selected so that the knots 24a', 24b' will grasp a respective strand 26a', 26b' that it surrounds with a force adequate that the knots 24a', 24b' will not slide within its respective knot 24a', 24b' oppositely to the tightening sliding direction as would permit enlargement of the loops 20a', 20b'.

The depicted knot configuration is also such that forces acting between the bone parts 12, 14 tending to move them away from each other acts on the sutures 22a', 22b' to cinch the knots 24a', 24b' even tighter. That is, the increased tension on the loops 20a', 20b' causes each knot 24a', 24b' on its associated suture 22a', 22b' to be cinched more tightly to thereby grasp its respective strand 26a', 26b' with a greater holding force to even more positively maintain the size of the loops 20a', 20b'.

The suture lengths defining the loops 20a', 20b' move in opposite directions around the second bone 14 or joining structure 40 thereat as the loops 20a', 20b' are reduced in size. Accordingly, regardless of which direction tension is applied to the loops 20a', 20b', through attempted relative movement of the bones 12, 14, the knots 24a', 24b' increase their grasping force on the surrounded, sliding suture length.

In other words, regardless of how forces are applied tending to displace the bones 12, 14 away from each other, including forces that produce asymmetrical loading on the combined loop CL, the knots 24a', 24b' at least one of: a) increase a grasping force on; and b) reconfigure surrounded suture lengths. In the latter case, the surrounded suture length is bent, or otherwise changed away from a linear configuration, and additionally becomes intermeshed with/wrapped against the knot to produce a greater frictional force that prevents slippage.

Referring to FIG. 5, it can be seen that the opposing sliding directions of the two loops 20a', 20b' provides an additional mechanism that allows the loops 20a', 20b' to easily be reduced in size when the free ends 44a', 44b' are pulled in the direction indicated by the arrow 46, but locks and prevents enlargement of the loops 20a', 20b' when tension is applied in the opposing direction, indicated by the arrow 42. The loop 20a' has an end portion 26e', with the strand 26b' on one side capable of sliding through the knot 24b', and the strand 26c' on the opposite side terminating at a point of fixation in the knot 24a'. Similarly, the loop 20b' has an end portion 26f' with the strand 26a' on one side capable of sliding through the knot 24a', and the strand 26d' on the opposite side terminating at a point of fixation in the knot 24b'. As the free ends 44a' and 44b' are drawn away from the knots 24b' and 24a', respectively, the forces are transmitted only to the sliding strand lengths 26a' and 26b' with fixed strand lengths 26c' and 26d' becoming unloaded, resulting in sliding of the strands 26a' and 26b' through the knots 24a' and 24b', and closure of the loops 20a', 20b'. In contrast, when load is applied to the end portions 26e' and 26f away from the knots 24a' and 24b', the load is applied to each strand on both sides of end portions 26e', 26f'. However, because the loop end portions 26e' and 26f' are wrapped around a second structure 30, a capstan effect is produced, amplifying the relatively low tensile loads in the sliding strands 26a', 26b' to resist relatively high tensile loads in the strand lengths 26d', 26c' respectively. Because of this, as force is applied in the direction of the arrow 42 to try to enlarge the loops, increasing loads in the strand lengths 26c' and 26d' can occur without slippage.

In FIG. 7, a component 48a' is shown between each of the knots 24a', 24b' and the first bone 12 with the suture assembly 18' in its operative state. The component 48a' is configured to block movement of each of the knots 24a', 24b' into and through the passage 28 in the first bone 12. The component 48a', as all components 48, is configured so that any exposed surfaces are curved/rounded to avoid tissue irritation.

As depicted, the component 48a' has a bone engaging side 56 and an opposite side 58. At least one, and in this case a single, through opening 60a extends between the bone engaging and opposite sides 56, 58. Two lengths of each of the first and second sutures 22a', 22b' extend through the opening 60a. The through opening 60a is configured so that the knots 24a', 24b' abut to the side 58 and cannot be wedged through the opening 60a as the tension on the loops 20a', 20b' increases.

Figure 9:
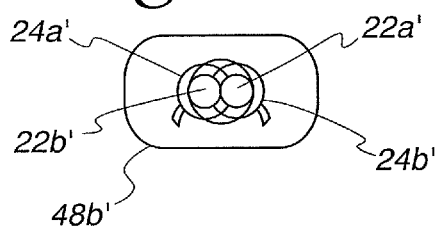
FIG. 9 is a view as in FIG. 8 wherein knots and portions of sutures are shown as they interact with the component.

In FIGS. 8-13, alternative configurations for the component 48a' are shown. In FIGS. 8 and 9, the component 48b' has a generally rectangular shape with a rounded peripheral edge 62b that is angled similarly to the corresponding edge 62a as shown on the component 48a' in FIG. 7. This avoids the creation of sharp corners that might irritate a patient's soft tissue.

The opening 60b has a circular shape with a diameter, relative to that of the material making up the sutures 22a', 22b', as shown in FIG. 9. As seen in FIG. 9, the knots 24a', 24b' collectively form a mass that has a substantially larger effective diameter than that of the opening 60b.

Figure 10:
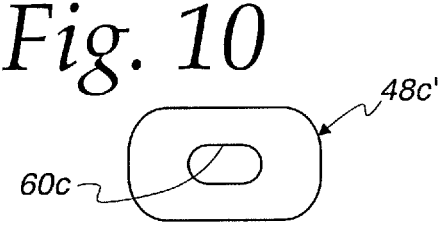
FIGS. 10 and 11 correspond respectively to FIGS. 8 and 9 and show a further alternative form of component acting between the knots and first bone.
Figure 11:
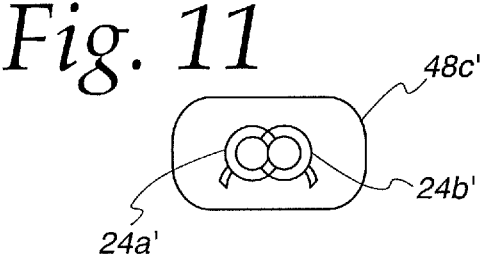

In FIGS. 10 and 11, a component 48c' is shown with an elongate opening 60c that interacts with the suture assembly 18, and the knots 24a', 24b', as shown in FIG. 11.

Figure 12:
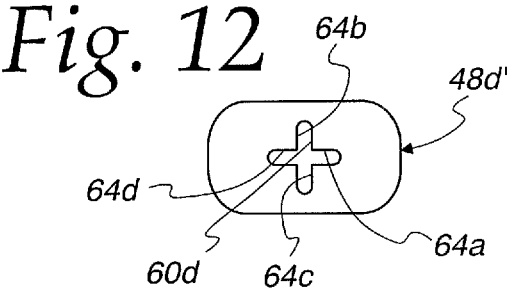
FIG. 12 is a view as in FIGS. 8 and 10 showing a further modified form of component acting between the knots and first bone.

In FIG. 12, a further form of the component is shown at 48d' with an opening 60d that has a shape of the letter "T" or "X". This opening shape produces arm portions 64a, 64b, 64c, 64d that will accommodate the diameter of the material of the sutures 22a', 22b', but will not pass the knots 24a', 24b'.

Figure 13:
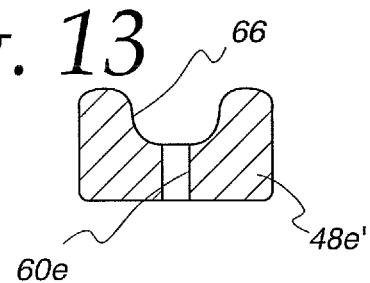
FIG. 13 is a cross-sectional view of a further modified form of component acting between the knots and first bone.

In FIG. 13, a further modified form of component is shown at 48e'. The component 48e' has an opening 60e that may be the same as any of the openings 60a-60d or with an alternative shape. The primary difference with the component 48e' is that a cup-shaped receptacle 66 is formed to accept part or all of the mass of the knots 24a', 24b'. With an overall rounded shape, the component 48e' may avoid any significant irritation of soft tissue while minimizing protruding exposure of the knots 24a', 24b'.

The component 54a', as shown in FIG. 7, has a body 68 with an elongate shape that is generally oval as viewed in FIG. 7. The body 68 has discrete, spaced openings 70a, 70b, respectively to accommodate a length of each of the sutures 22a', 22b'. Between the openings 70a, 70b, a wall 72a is formed around which the loop portions 52a', 52b' wrap to allow the loop portions 52a', 52b' to produce a bearing force on the second bone 14 to which the body 68 abuts that urges the second bone 14 towards the first bone 12 as the loops 20a', 20b' are restricted/tensioned.

The significance of the overall shape of the body 68 shown will be explained below. All edges are rounded to avoid irritation of soft tissue.

Figure 14:
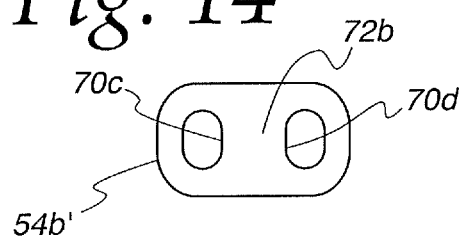
FIG. 14 is an end view of one form of component, as shown in FIG. 7, for cooperating between suture assembly loops and the second bone.
Figure 15:
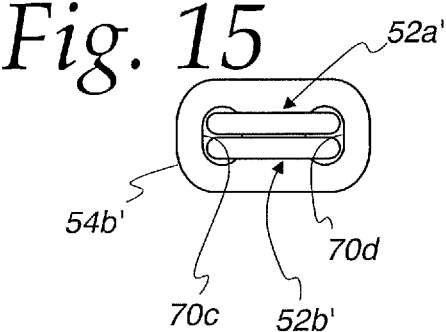
FIG. 15 is a view as in FIG. 14 with the cooperating loops shown.

Alternative forms of the component 54a' are shown in FIGS. 14-17. In FIGS. 14 and 15, the component 54b' has two generally oval, spaced openings 70c, 70d with a wall 72b therebetween against which the loop portions 52a', 52b' independently wrap, as shown in FIG. 15.

Figure 16:
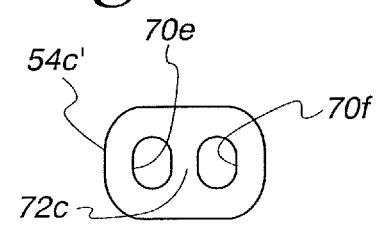
FIGS. 16 and 17 are views corresponding to those in FIGS. 14 and 15 and showing a modified form of component that interacts with the loops in a different manner.
Figure 17:
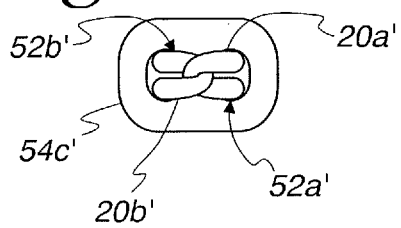

In FIGS. 16 and 17, the component 54c' has generally the same configuration as the component 54b' with the exception that the openings 70e, 70f are closer together to define a narrower wall 72c. The loops 20a', 20b' extend, each through the other, at the loop portions 52a', 52b' and are wrapped against the wall 72c as shown in FIG. 17. With this arrangement, the loops 20a', 20b' independently pass through only one of the openings 70e, 70f.

In each of these embodiments, the components 54 become captive between the loop portions 52', 52b' and the second bone 14. Each of the components 54, as shown with the exemplary component 54a' in FIG. 7, has a bone engaging side 74 and an opposite side 76, with the loop portions 52a', 52b' bearing against the wall 72a at the opposite side 76. A capstan effect results where the loop portions 52a', 52b' wrap against the components 54. This further aids in avoiding sliding of the sutures 22a', 22b' in their respective surrounding knots 24b', 24a' under load.

In FIGS. 18-20, an introduction assembly at 78 is depicted for advancing the loops 20a', 20b' on the suture assembly 18' with the loops 20a', 20b' engaging the component 54a'. The introduction assembly 78 includes a cylindrical housing 80 defining an elongate receptacle 82 for the suture assembly 18. The elongate component 54a' is turned so that its length aligns with the axis 84 of the receptacle 82, as shown in FIG. 18. The component 54a' projects slightly from the leading end 86 of the housing 80. A plunger 88 engages at one of the lengthwise ends 90 of the component 54a'.

With the introduction assembly 78 engaged with the suture assembly 18 as shown in FIG. 18, the leading end 86 of the housing and component 54*a*' can be used to cooperatively guide the introduction assembly 78 and suture assembly 18 in the first direction, indicated by the arrow 42, into and through the passage 28 in the first bone 12 and a passage 92 of like diameter in the second bone 14. The introduction assembly 78 with the engaged suture assembly 18 has an effective cross-sectional area that can be accommodated by a relatively small diameter opening defining the passages 28, 92.

Once the FIG. 19 position for the housing 80 is realized, the plunger 88 can be advanced in the direction of the arrow 94 within the receptacle 82, which causes the component 54*a*' to advance further in the first direction and pivot in the direction of the arrow 96 towards the FIG. 20 position. By then backing the introduction assembly 78 out of the bone passages 92, 28, the loops 20*a*', 20*b*' will be drawn in the second direction, as indicated by the arrow 46 to present the surface 74 of the body 68 against the second bone 14.

Figure 21:
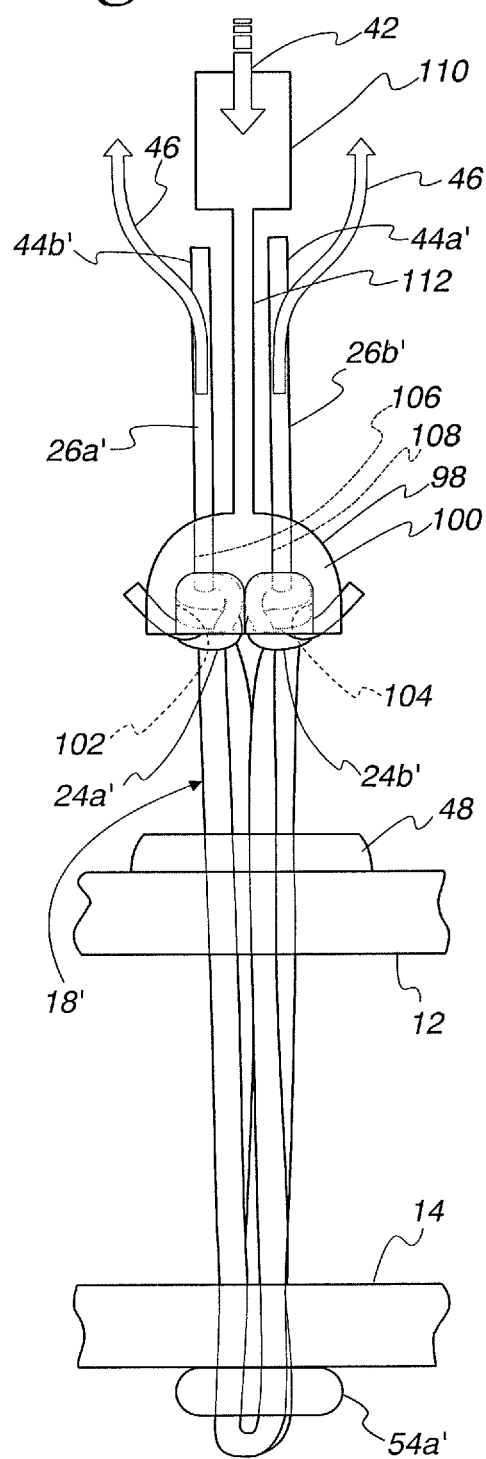
FIG. 21 is a view as in FIG. 7 with the suture assembly in its operative and starting state and with a knot pusher engaged.
Figure 22:
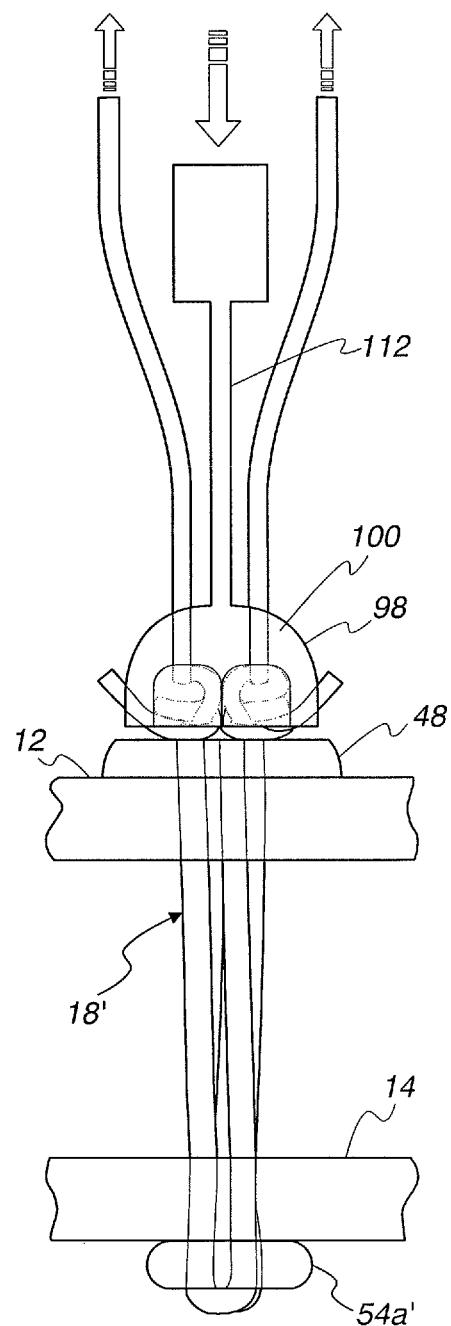
FIG. 22 is a view as in FIG. 21 wherein the knot pusher is manipulated to cinch the knots.

Once this occurs, the suture assembly 18 can be changed from its operative and starting state, as shown in FIG. 21, to its operative and engaged state, as shown in FIG. 22. While it is possible to change the state of the suture assembly 18' manually and without any special tool, for convenience purposes, a knot pusher 98 is provided. The knot pusher 98 has a generally cup-shaped housing 100 with spaced receptacles 102, 104 for the knots 24*a*', 24*b*' respectively. Channels 106, 108 extend from the receptacles 102, 104, respectively, fully through the housing 100 to accommodate the strands 26*a*', 26*b*', respectively. Using the same concepts, in an alternative form, a single receptacle and channel might be used. A pressing member 110 connects to the housing 100 through a narrow stem 112.

In the FIG. 21 position, the pressing member 110 is shown stabilizing the knots 24*a*', 24*b*' as the strand parts 44*a*', 44*b*' are drawn in the second direction, as indicated by the arrows 46. The pressing member 110 will follow the resulting shifting of the knots 24*a*', 24*b*' in the first direction, as indicated by the arrow 42, until the FIG. 22 state is realized.

Figure 23:
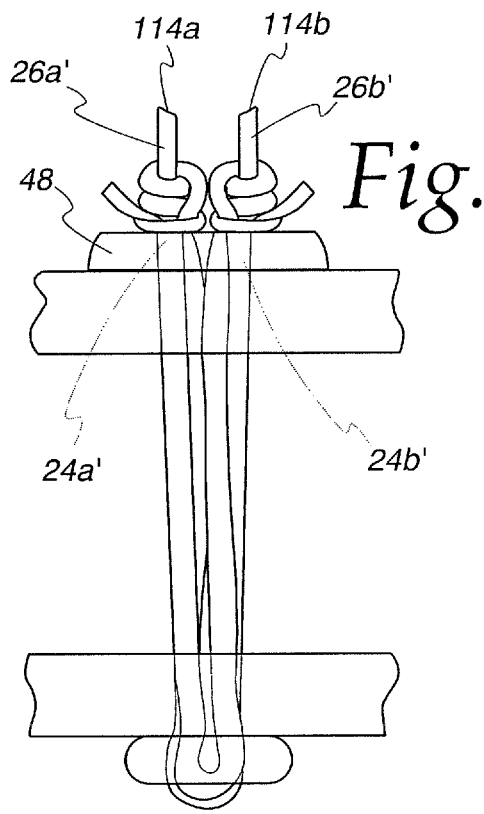
FIG. 23 is a view as in FIGS. 21 and 22 wherein the knot pusher is separated and parts of the sutures that are drawn are severed.

Thereafter, the knot pusher 98 is separated and the strands 26*a*', 26*b*' severed, as shown in FIG. 23, to produce standing ends 114*a*, 114*b* that do not project significantly beyond the knots 24*a*', 24*b*'.

It is noted that the component 48 is interposed between the knots 24*a*', 24*b*' and the first bone 12. While the component 48 is not seen in FIGS. 18-20, it can be incorporated into the suture assembly 18 before being operatively engaged with the introduction assembly 78. The elongate component 48 can be reoriented during this process in the same way that the component 54*a*' is reoriented to allow introduction into and withdrawal from the receptacle 82 on the introduction assembly housing 80.

Certain connections with the second bone 14 may not require advancement of the loops 20*a*', 20*b*' through the second bone. However, the same basic assembly steps would be performed with such different embodiments. Though not specifically shown it would be obvious to one skilled in the art to secure the loop 20 to an anchoring structure on the surface of the second bone 14, or partially within the second bone 14.

Figure 24:
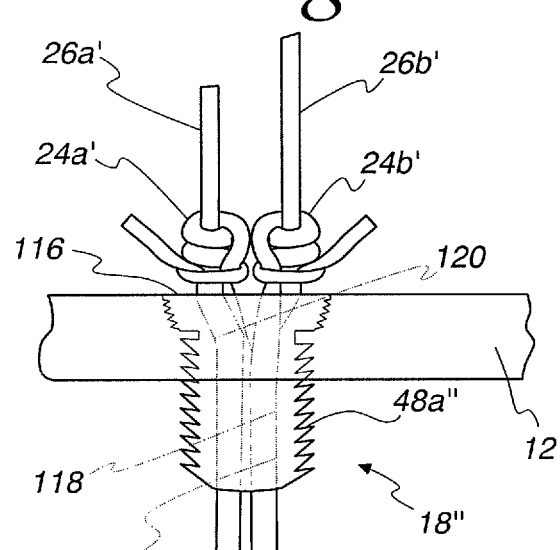
FIG. 24 is a view as in FIG. 21 without the knot pusher and with a different form of component acting between the knots and first bone.
Figure 25:
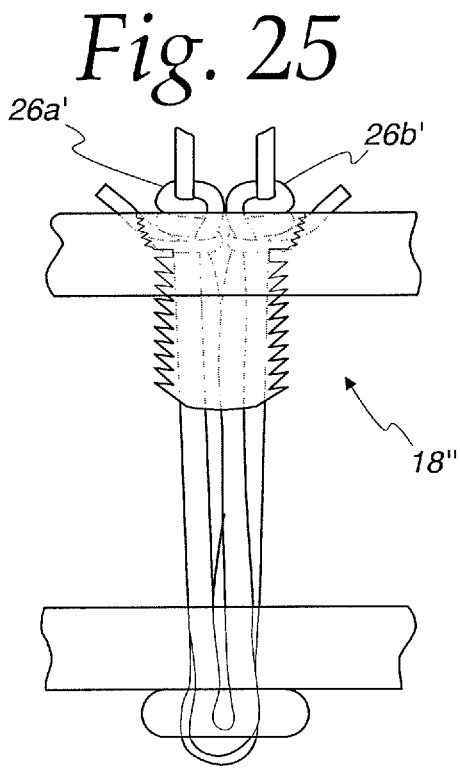
FIG. 25 is a view as in FIG. 24 wherein the knots have been cinched and the drawn portions of the sutures have been severed.

In FIGS. 24 and 25, a further modified form of suture assembly is shown at 18". The suture assembly 18" differs from the suture assembly 18' primarily by reason of the configuration of the component 48*a*", which functions as an anchor component. The component 48*a*" is in the form of a threaded bone screw with a through opening 60*a*". A hole is drilled in the first bone 12 to allow threaded implantation of the component 48*a*". The loops 20*a*', 20*b*' are directed through the opening 60*a*" to prepare the suture assembly 18" for use. The operative and starting state for the suture assembly 18" is shown in FIG. 24. The stabilized knots 24*a*', 24*b*' are shifted toward the first bone 12 as the strands 26*a*', 26*b*' are drawn away from the first bone 12 to secure the suture assembly 18.

The trailing end 116 of the component 48*a*" may be a planar surface to which the knots 24*a*', 24*b*' abut when they are fully cinched. More preferably, the configuration is as shown in FIG. 24. The through opening 60*a*" has a constant diameter portion 118. An opening portion 120 near the trailing end 116 has a diameter that tapers from the trailing end 116 up to the portion 118, thereby to define a truncated conical surface that bounds a receptacle for the knots 24*a*', 24*b*' and supports the knots 24*a*', 24*b*' when fully cinched. The knots 24*a*', 24*b*' are shown fully seated in FIG. 25.

As shown in FIG. 26, the opening 60*a*" may cause standing ends 122*a*, 122*b* on the strands 26*a*', 26*b*', after severance thereof, to be angled with respect to the line of tension of the loops 20*a*', 20*b*', as indicated by the double-headed arrow 124. With this relationship, as the knots 24*a*', 24*b*' are cinched, they tend to pinch the angled standing ends 122*a*, 122*b*, thereby to provide greater resistance to sliding of the knots 24*a*', 24*b*' along the strands 26*a*', 26*b*' that might slacken the loops 20*a*', 20*b*'. Further, the reconfiguration of the knots 24*a*', 24*b*' under the cinching forces causes the knot material and strands 26*a*', 26*b* to intermesh and be held tighter against each other over an extended, non-straight length to enhance frictional holding forces that prevent slippage.

The cross-sectional configuration of the opening 60*a*" may take, for example, shapes such as those for the openings 60*b*, 60*c*, 60*d*, as shown in FIGS. 8, 10, and 12, or another shape.

In FIG. 27, the suture assembly 18" is shown with another system component in the form of a plate 126. The plate 126 is configured conventionally to be fixed to stabilize separate parts 128, 130 of the first bone 12 in the vicinity of a fracture.

The component 48*a*" has optional threads 132 to engage within a threaded opening 134 on the plate 126. The component 48*a*" is shown with two sets of optional threads—one 132 for engagement with the plate 126 and one 135 to securely anchor the component 48" in the first bone 12. The component 48*a*" might be made without the set of threads 132 if used without a plate, as in FIG. 26, however a universal construction can be used for both applications.

Figure 28:
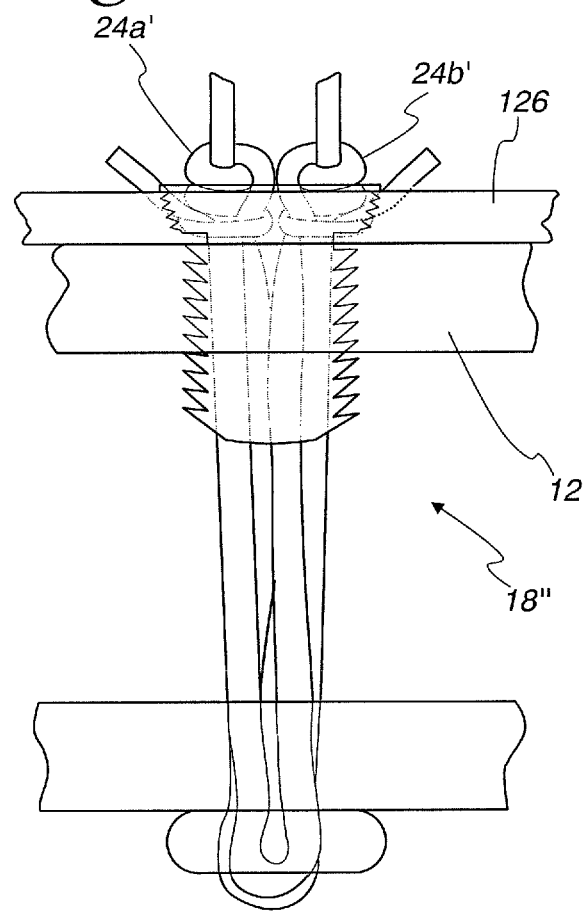
FIG. 28 is a view as in FIG. 27 wherein the plate is attached to a first bone, the knots are cinched, and the drawn portions of the suture are severed.

The suture assembly 18" can be used otherwise in the same manner as the other versions of the suture assembly 18 described above, with the final operative and assembled state for the suture assembly 18" shown in FIG. 28.

It is also contemplated that the loops 20*a*', 20*b*' might be engaged at the second bone 14 through a procedure performed through the second bone 14 as shown in FIGS. 29-33.

Figure 29:
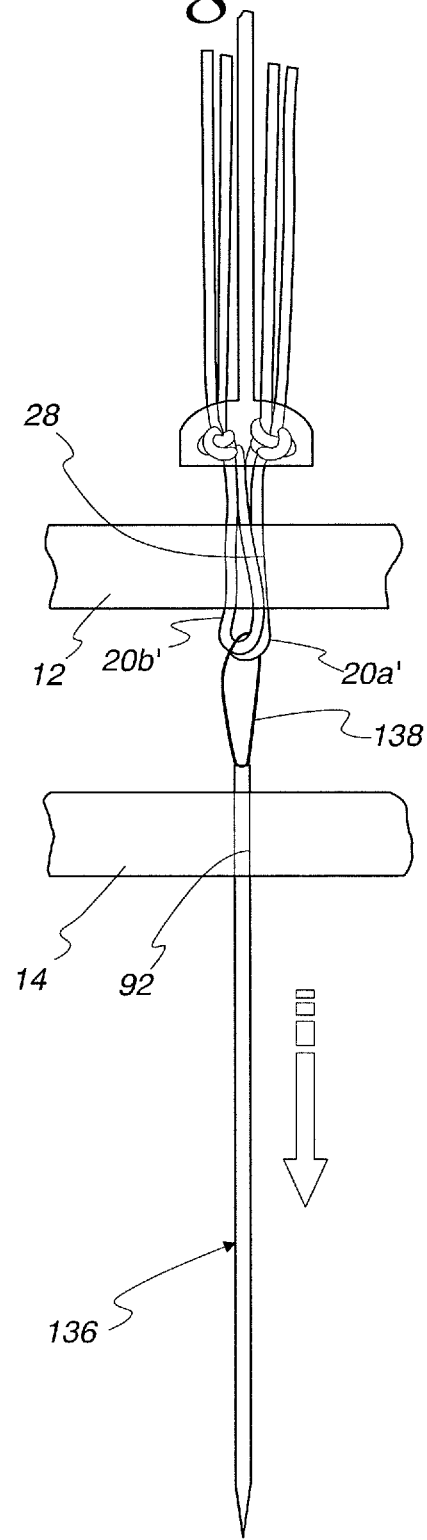
FIG. 29 is an elevation view of the inventive suture assembly with an assembly instrument attached to the suture assembly loops and advanced to draw the suture assembly loops through the first bone.
Figure 30:
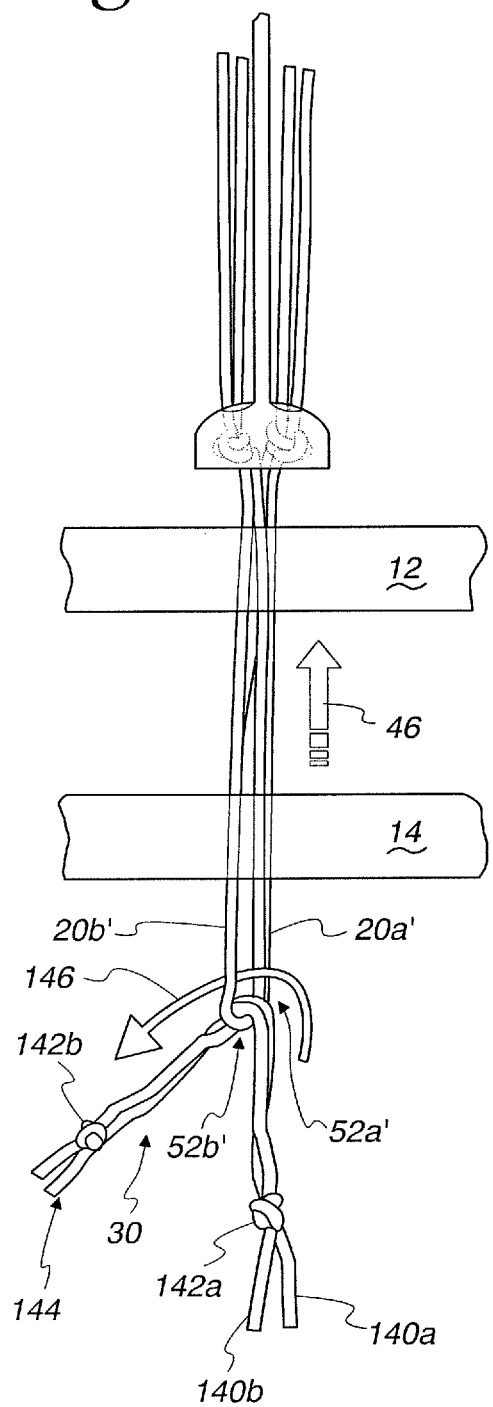
FIG. 30 is a view as in FIG. 29 wherein the suture assembly loops are drawn through both the first and second bones and a loop forming structure is attached to the loops.

As shown in FIG. 29, an assembly instrument 136 with a drawing ring 138 may be engaged with the loops 20*a*', 20*b*' to allow them to be drawn consecutively through the passage 28 in the first bone 12 and passage 92 in the second bone 14 so that the loop portions 52*a*', 52*b*' are exposed beyond the second bone as shown in FIG. 30. This allows connection of the loops 20*a*', 20*b*' to the aforementioned anchor structure 30 that is connected from the location adjacent to the second bone 14. The structure 30 is not limited to the structure shown in FIGS. 30-33. The exemplary structure 30 is in the form of a pair of sutures 140*a*, 140*b* that have coextensive lengths and are tied in a manner to define spaced knots 142*a*, 142*b*.

Figure 31:
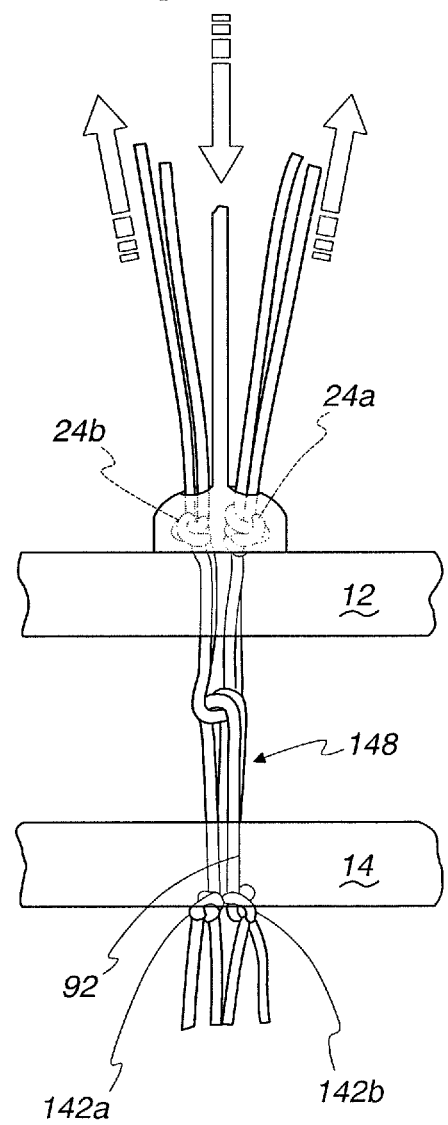
FIG. 31 is a view as in FIG. 30 wherein the suture assembly loops are restricted, using a knot pusher to cause the suture assembly loops to be held by the loop forming structure on the second bone as the knots are cinched.

By directing an end 144 of the structure 30 through the loops 20*a'*, 20*b'*, as indicated by the arrow 146 in FIG. 30, the loops 20*a'*, 20*b'* can be moved in the aforementioned second direction, as indicated by the arrow 46, to draw the loop portions 52*a'*, 52*b'* and a portion of the structure 30 back through the passage 92 in the second bone 14. The knots 142*a*, 142*b* abut to the second bone 14, as shown in FIG. 31, to thereby block further movement so that the structure 30 defines an anchoring loop 148. The loops 20*a'*, 20*b'* and 148 extend each through the other and cooperate to limit movement of the first and second bones 12, 14 away from each other.

Figure 32:
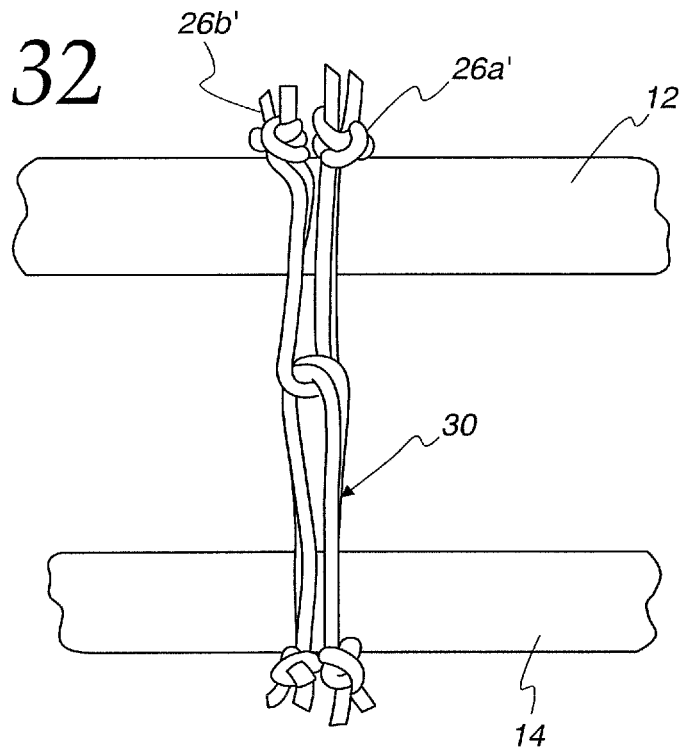
FIG. 32 is a view as in FIG. 31 wherein the drawn parts of the sutures are severed.

The knots 24*a*, 24*b* are thereafter cinched as in earlier embodiments with the final configuration for the system shown in FIG. 32. It should be noted that although the drawings depict the structure 30 in the form of two sutures and two knots, alternative configurations are contemplated, such as a single suture extended through the loops 20*a'*, 20*b'* and tied into a single knot with a size greater than the channel 92.

Figure 33:
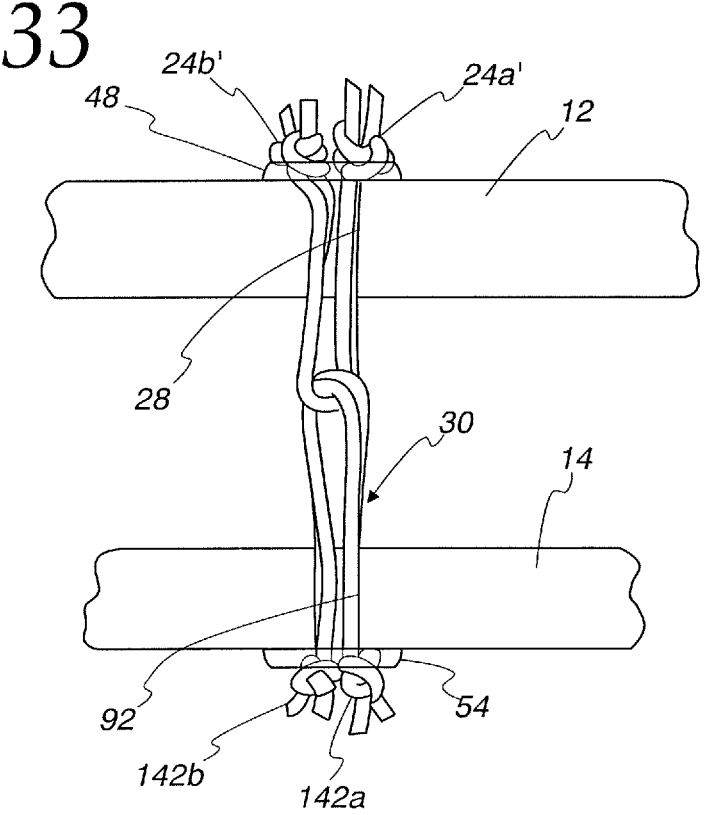
FIG. 33 is a view as in FIG. 32 wherein components are provided between each of: a) the knots and first bone; and b) loop forming structure on the second bone and the second bone.

With this embodiment, as in all embodiments, the use of separate components to block suture/knot movement is optional. As shown in FIG. 33, components 48, 54 with any of the various described constructions or another construction, can be used to block passage of the knots 24*a'*, 24*b'* and 142*a*, 142*b* through their respective passages 28, 92.

It should be understood, as noted above, that the structure 30 could vary considerably from the depicted form. For example, a fixed fastener might be provided on the second bone 14 to serve as an anchor for the loops 20*a'*, 20*b'*.

As mentioned with respect to the embodiment shown in FIG. 26, enhanced knot holding may be achieved by causing a pinching action between the knot 24*a'*, 24*b'* and its associated strand 26*a'*, 26*b'*. Different forms of components with this feature are shown in FIGS. 34-40.

Figure 34:
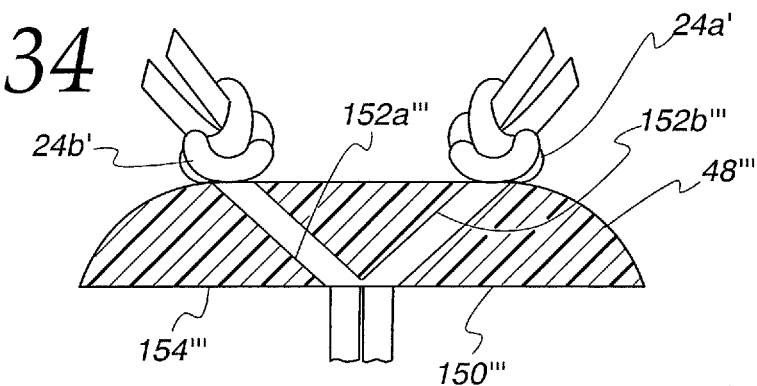
FIG. 34 is an enlarged, cross-sectional view of a modified form of component cooperating between the knots and first bone.

In FIG. 34, a component 48''' has a body 150''' with openings 152*a'''*, 152*b'''* that accommodate suture lengths extending from the knots 24*a'*, 24*b'*. The openings 152*a'''*, 152*b'''* converge to cooperatively define an opening configuration at the surface 154''' in the shape of the number "8".

Figure 35:
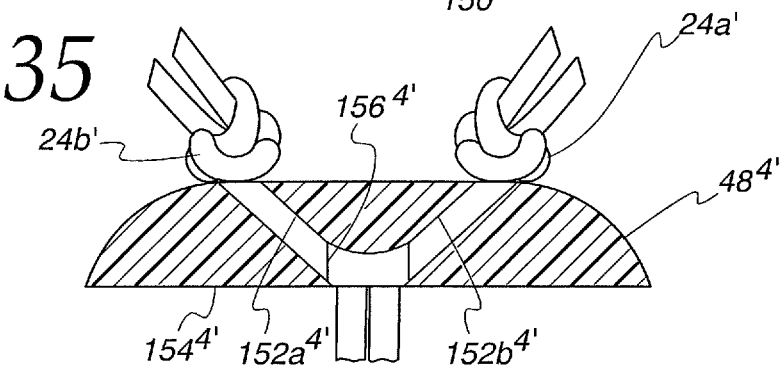
FIG. 35 is a view as in FIG. 34 of a further modified form of component.

The component 48$^{4'}$ in FIG. 35 differs from 48''' primarily in that the openings 152*a*$^{4'}$, 152*b*$^{4'}$ converge to a chamber 156$^{4'}$ that has a continuous oval shape at the surface 154$^{4'}$.

Figure 36:
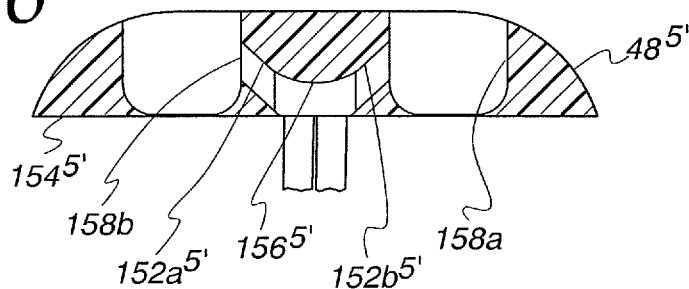
FIG. 36 is a view as in FIGS. 34 and 35 of a still further modified form of component.
Figure 37:
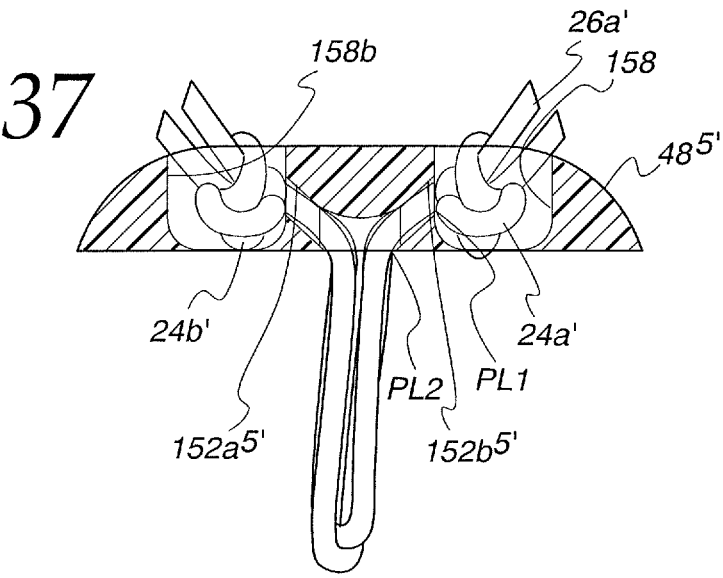
FIG. 37 is a view as in FIG. 36 with knotted sutures in place.

In FIGS. 36 and 37, the component 48$^{5'}$ has converging openings 152*a*$^{5'}$, 152*b*$^{5'}$ with a chamber 156$^{5'}$ therebetween and which defines an oval exit opening at the surface 154$^{5'}$.

With this construction, the cinched knots 24*a'*, 24*b'* sit in receptacles 158*a*, 158*b*, respectively. As a result, the suture portions extending from the knots 24*a'*, 24*b'* bend to enter the openings 152*a*$^{5'}$, 152*b*$^{5'}$ and further bend where they exit the component 48$^{5'}$ through the chamber 156$^{5'}$.

As can be seen most clearly in FIG. 37, the exemplary strand 26*a'*, that is surrounded by the knot 24*a'*, has two relatively sharp bends, thereby forming pinch locations PL1, PL2 that inhibit relative sliding movement between the strand 26*a'* and the knot 24*a'*.

In FIGS. 38-40, a further form of component is shown at 48$^{6'}$. The component 48$^{6'}$ has a body 160 with spaced walls 162, 164 between which a cavity 166 is formed.

The wall 164 has a single through opening 168 through which two lengths of the first suture 22*a'* extend and two lengths of the second suture 22*b'* extend. The first and second knots 24*a'*, 24*b'* shift at least partially into the cavity 166 upon being cinched and are blocked by curved edges 170*a*, 170*b* each defined partially by the walls 162, 164.

In a still further alternative form, as shown in FIGS. 41-44, a counterbore 172 is formed at the entry to the passage 28 in the first bone 12. A component 48$^{7'}$ is provided in the form of an insert that nests in the modified passage 28. The component 48$^{7'}$ is configured to produce spaced receptacles 176*a*, 176*b*, each to accommodate one of the knots 24*a'*, 24*b'*. Lengths of each of the first and second sutures 22*a'*, 22*b'* extend from the chambers 176*a*, 176*b* through openings 178*a*, 178*b* at diametrically opposite locations relative to the passage access end, and from there are redirected axially through a cylindrical opening 180 that is coaxial with the passage 28.

With this construction, the recessing of the knots 24*a*, 24*b* is accomplished while at the same time the sutures are caused to bend in the region of the knots 24*a*, 24*b*, which inhibits sliding of the knots 24*a*, 24*b* along lengths of the sutures 22*a'*, 22*b'* that they surround.

It is contemplated that with any of the above structures, components can be interchanged. With any combination of the above components, a method can be carried out, as shown in flow diagram form in FIG. 45, to control a relationship between first and second bones.

As shown at block 184, a system as described above is obtained.

As shown at block 186, with the suture assembly in a starting state, wherein the first and second knots are preformed, portions of the first and second loops defined by the suture assembly are directed through at least one passage in the first bone.

As shown at block 188, the first and second loops are thereafter engaged with the second bone.

As shown at block 190, with the first and second loops engaged, parts of the first and second strands are drawn, while stabilizing the first and second knots, to thereby produce a tension on the first and second loops selected to maintain a desired relationship between the first and second bones.

Figure 48:
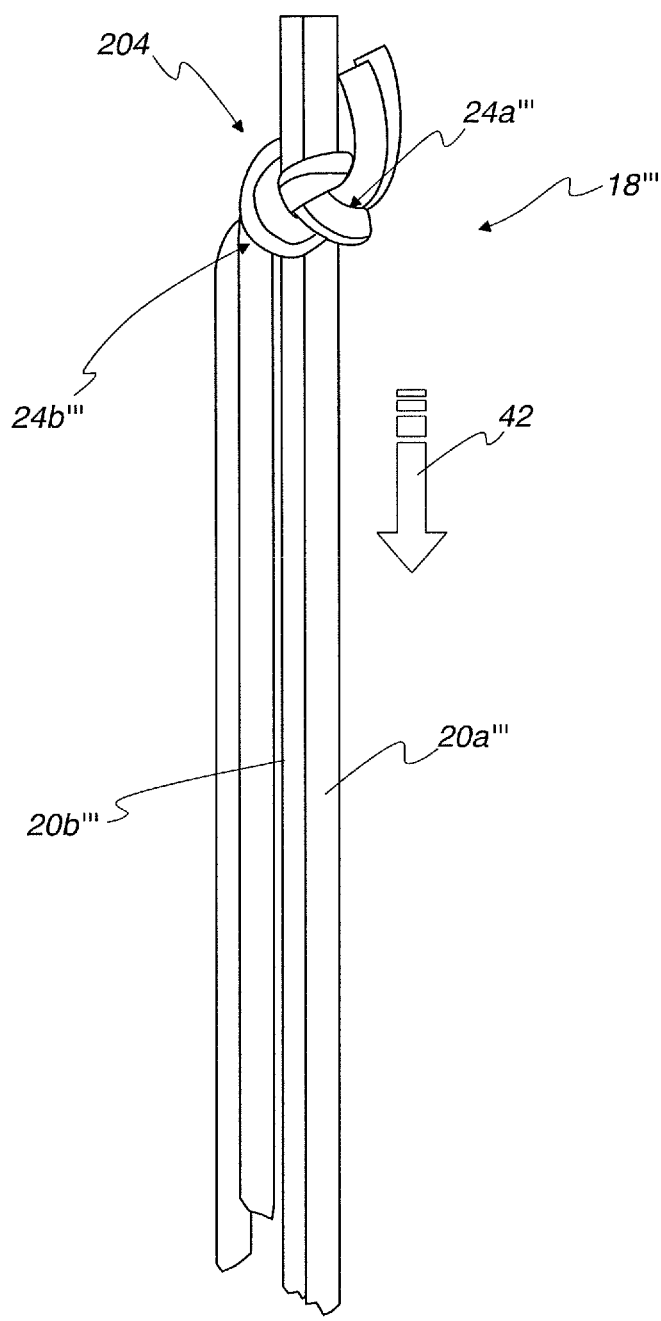
FIG. 48 is a view as in FIG. 47 wherein the double strand knot is cinched.

In FIGS. 46-48, a further modified, and preferred, form of suture assembly, according to the present invention, is shown at 18'''. The suture assembly 18''' includes first and second sutures 22*a'''*, 22*b'''* that are formed to produce knots 24*a'''*, 24*b'''*.

In this embodiment, the first and second sutures 22*a'''*, 22*b'''* have strand lengths 202*a'''*, 202*b'''* that are maintained together and formed in the same manner to produce first and second knots 24*a'''*, 24*b'''* so that the first and second knots 24*a'''*, 24*b'''* are combined to produce a double strand knot at 204 with the suture assembly 18''' in the operative state. By combining both strand lengths 202*a'''*; 202*b'''* into a single knot, asymmetrical tension upon tightening the system is avoided. Furthermore, a greater discrepancy in the effective diameter of the composite knot 204 and strands 20*a'''*, 20*b'''* allows greater tolerance in variation in the size of the passage 28 without concern of passage of the knot 204 into the passage 28.

More specifically, the strand lengths 202*a'''*, 202*b'''* are formed to produce any of the aforementioned knots—half hitch, rolling hitch, adjustable bend, midshipman's hitch, and adjustable hitch. The invention, however, is not limited to any of these knot configurations. As depicted in FIG. 47, the strand lengths 202*a'''*, 202*b'''* are formed to produce an adjustable bend knot, as described in detail above, with respect to FIG. 4.

With this construction, each of the first and second knots 24*a'''*, 24*b'''* surrounds lengths 206*a'''*, 206*b'''* of each of the first and second sutures 22a''', 22b'''. These lengths 206a''', 206b''' slide through the composite knot 204 formed by knots 24a''', 24b''' as the first and second sutures 22a''', 22b''' are manipulated to reduce sizes of restrictable loops/sub-loops 20a''', 20b''', respectively defined by the first and second sutures 22a''', 22b'''.

Loop size reduction is effected in substantially the same manner as with previously described embodiments. That is, with the knots 24a''', 24b''' stabilized, suture parts 208a''', 208b''' are drawn oppositely to the aforementioned first direction, as indicated by the arrow 42, as an incident of which the double strand knot 204 shifts toward the first bone 12 in the aforementioned first direction.

As shown schematically in FIG. 46, the first and second sutures 22a''', 22b''' can cooperate directly with the first bone 12, as shown in dotted lines, or may cooperate with the first bone through structure shown schematically at 210. This structure 210 is intended to encompass all of the structures described above with the different forms of the suture assembly 18, 18', 18'', as well as that described in detail hereinbelow and others that would be obvious to one skilled in the art with the teachings herein in hand. The structure 210 may incorporate one or more components made, for example, from at least one of: steel, titanium alloy, titanium, or another metal. Alternatively, the material of construction may be PEEK or another plastic or composite material.

Similarly, the restrictable loops 20a''', 20b''' may cooperate directly with the second bone 14, as shown in dotted lines in FIG. 46, or may cooperate with the second bone 14 through structure shown schematically at 212. The structure 212 is intended to encompass all structures described hereinabove for the suture assemblies 18, 18', 18'' and virtually an unlimited number of others within the schematic showing in FIG. 2. The structure 212 may include components made from the same materials making up one or more of the components of the structure 210.

The suture assembly 18''' incorporates aspects of each of the suture assemblies 18, 18', shown respectively in FIGS. 4 and 6. The sutures 22a''', 22b''' each independently forms restrictable loops 20a''', 20b''', respectively, while at the same time, the sutures 22a''', 22b''' are integrated to have characteristics of the structure in FIG. 6. The double strand knot configuration, by reason of the more intricate intermeshing and bending of the sutures 22a''', 22b''', produces more "pinch points" and dissipation of tension in the suture that resist slippage and tighten as tension is placed upon the restrictable loops 20a''', 20b''', tending to enlarge the same.

The double strand knot 204 will generally occupy a volume less than that of the combined volume of the knots 24a', 24b', separated as in FIG. 6. At the same time, the double strand knot 204 produces a mass that is large enough that it can be readily blocked from moving through one or more passages in the first bone 12, through which strands of the first and second sutures 20a''', 20b''' pass to allow engagement with the second bone 14 and/or the structure 212 thereon.

The above construction is significant from the standpoint that with certain of the embodiments described above, a single passage through the first bone with a dimension adequate to accommodate four strand lengths on separate restrictable loops would normally be large enough that each of two separately formed knots might have an appreciable tendency to pass therethrough. With the double strand knot, a passage with a circular cross-section can readily accept four suture strands without concerns about passage therethrough of the double strand knot 204, even in the absence of using any of the aforementioned structures 210.

Further, by reason of the aforementioned interengagement of the sutures 22a''', 22b''' within the double strand knot 204, it has been found that instead of using the depicted three loops with a half hitch, as in FIGS. 4 and 47, two loops with a half hitch with this knot configuration have proven adequate during testing.

The suture assembly 18''' lends itself to being used with a number of different structures, corresponding to that identified schematically at 210 in FIG. 46, and shown in specific alternative forms in FIGS. 49-55. The structures are exemplary in nature only, and while particularly adaptable to the double strand knot 204, are usable with any of the suture assembly constructions as described hereinabove.

As shown in FIG. 47, one of the loops 20a''', 20b''', and in this case the loops 20a''', is flipped to produce a crossing region at CR. The loops/sub-loops 20a''', 20b''' together make up a restrictable loop structure defining a combined loop CLA. Drawing of the free ends/suture parts 208a'-, 208b''' in the direction of the arrow 46, by reason of the flipped arrangement of the loop 20a''', results in tensioning of the suture loops 20a''', 20b''' in opposite directions. As a result, when tension is applied to the combined loop CLA in either of two opposite directions, each of the 24a''', 24b''' will at least one of: a) grasp the suture lengths 206a''', 206b''' that it extends around with a greater force; and b) reconfigure the suture lengths 206a''', 206b''' that it extends around to resist sliding movement of the suture lengths 206a''', 206b''' in the knots 24a''', 24b'''.

Figure 49:
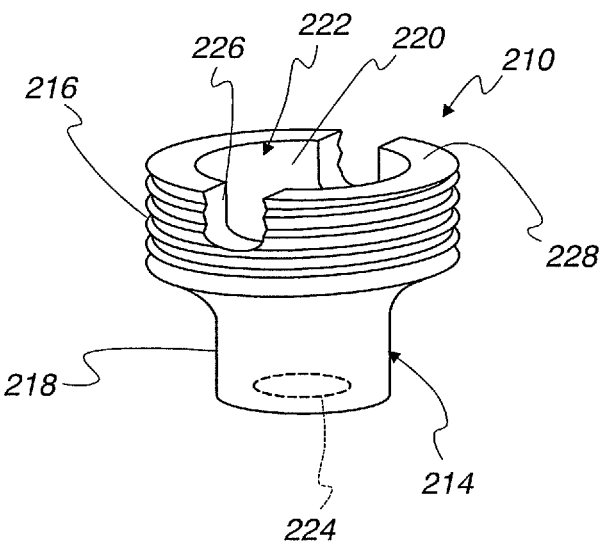
FIG. 49 is a perspective view of one form of blocking structure that cooperates between one or more knots on the inventive suture assembly at the first bone.

In FIG. 49, a blocking structure 210 is shown having a body 214 with a stepped outer diameter. A larger diameter portion 216 is threaded and blends into an unthreaded, smaller diameter portion 218. The body 214 has a surface 220 that bounds a cup-shaped receptacle 222 that is contiguous with an opening 224 in the smaller diameter portion 218 of the body 214, which opening 224 is dimensioned to be slightly larger than the combined diameters of the suture strands extending therethrough. The double strand knot 204 or the separate knots 24a', 24b' seat within the cup-shaped receptacle 222.

The body 214 has a slot 226 to accommodate a conventional screwdriver that can be used to turn the body 214 to threadably engage the larger diameter portion 216 with the first bone 12 or a plate thereon.

The top edge 228 of the body 214 can be advanced into the first bone 12 to be flush with the exposed surface thereon or, alternatively, may be recessed to avoid protrusion of any portion of the knots 24a', 24b', 204 that nest in the receptacle 222.

Figure 50:
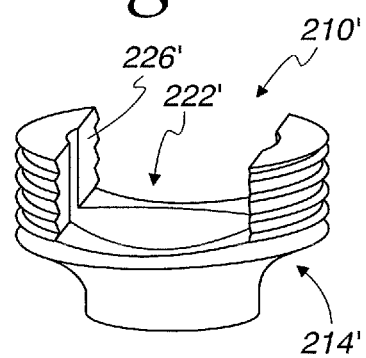
FIG. 50 is a perspective view of another form of the inventive blocking structure for use at the first bone.

FIG. 50 shows a blocking structure 210' that is modified from the structure 210 principally by enlarging the corresponding slot 226' to produce a larger volume to accommodate the knots 24a', 24b', 204. This structure is designed for use preferably with a specific form of driving mechanism, that is an alternative to a conventional screwdriver, as described hereinbelow with respect to FIGS. 57-59.

Figure 51:
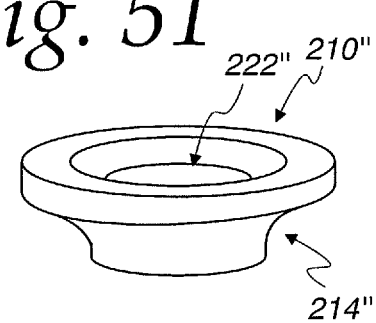
FIG. 51 is a perspective view of another form of the inventive blocking structure.

In FIG. 51, a modified form of blocking structure is shown at 210''. The blocking structure 210'' has an unthreaded, tapered body 214'' defining a receptacle 222'' with the general function of the blocking structure 210'' being the same as described for the blocking structures 210, 210'. By reason of making the body 214'' unthreaded, the blocking structure 210'' can be placed in a slotted or circular screw hole or directly against the first bone 12.

Figure 52:
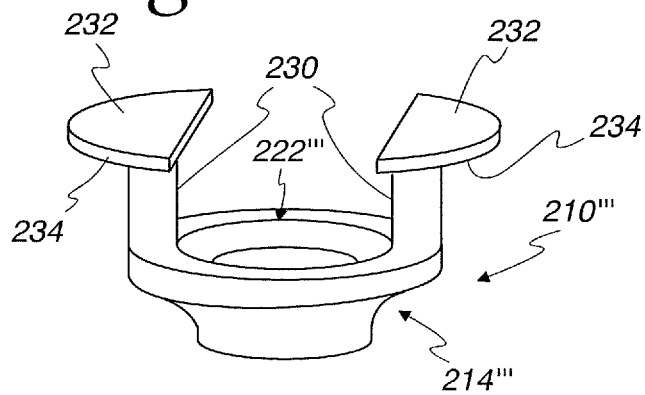
FIG. 52 is a perspective view of another form of the inventive blocking structure.

FIG. 52 shows a blocking structure 210''' that is similar to the blocking structure 210'' in FIG. 51, but additionally incorporates depth controlling arms 230, which are integrally formed therewith at diametrically opposite locations.

The arms 230 each has a transverse tab 232 projecting to beyond the diameter of the body 214'''.

With this arrangement, a bore can be formed in the first bone 12 and/or a plate thereon with a diameter to accommodate the diameter of the body 214''' and a depth to accommodate the full axial extent of the arms 230. Surfaces 234 on each tab 232 block movement of the blocking structure 214''' into the accommodating bore, thereby to consistently maintain the body 214''' at a desired depth that will accommodate preferably the full volume of the knots 24a', 24b', 204 in a receptacle 222'''.

Figure 53:
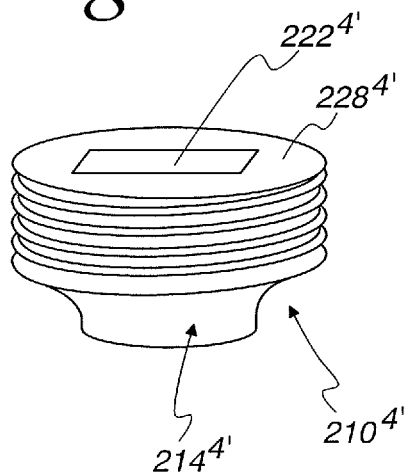
FIG. 53 is a perspective view of a still further form of the inventive blocking structure.

FIG. 53 depicts a blocking structure $210^{4'}$ that has similarities to the blocking structures 210, 210'. The blocking structure $210^{4'}$ has a body $214^{4'}$ that is configured to be threadably directed into a bore through the first bone 12 and/or a plate thereon into a flush or a recessed position. The receptacle $222^{4'}$ is elongate to accommodate an installation tool such as a screwdriver. The knots 24a', 24b' 204 will normally not extend fully into the receptacle 224'. Instead, the knots 24a', 24b', 204 will bear on the top edge $228^{4'}$ of the body $214^{4'}$.

In FIGS. 54 and 55, a blocking structure is shown at $210^{5'}$ that incorporates a body $214^{5'}$, generally the same as the body $214^{4'}$. A depth control assembly 236 is separately attached to the body $214^{5'}$ to produce a configuration generally as shown in FIG. 52, wherein the depth of the placement of the body $214^{5'}$ can be consistently controlled. The depth control assembly 236 defines a seat 237 for the body $214^{5'}$.

With the embodiments shown in FIGS. 49, 51, and 53-55, the receptacles 222, 222''', $222^{4'}$, and $222^{5'}$ may be dimensioned so that the knots 24a', 24b', 204 do not extend fully thereinto. Thus, the depth of the bodies 214, 214''', $214^{4'}$, $214^{5'}$ within their respective bones may be controlled so that the bodies 214, 214''', $214^{4'}$, $214^{5'}$ are recessed at least to a degree that will accommodate the knots 24a', 24b', 204 so that the knots 24a', 24b', 204 do not project outwardly from the exposed surface of the first bone 12 and/or plate thereon.

Those structures 210 that include a component, such as the body 214, defining a receptacle to accept significant portions of the knots 24a', 24b', 204 are, in a preferred form, configured to accept a majority of the knot volume, and in one form, the entirety of the volume of the knot(s). The body 214' in FIG. 50 is configured in this manner.

While in FIG. 49 a slot 226 is shown to accommodate a conventional type screwdriver, the invention contemplates other types of fittings 238, as shown schematically on the structure 210 in FIG. 56, that can cooperate with a driving component 240 on a turning tool 242. The schematic showing in FIG. 56 is intended to encompass any structure that makes a keyed connection between the tool 242 and the structure 210 to allow the required turning of the component on the structure 210 through manipulation of the tool 242.

In one exemplary form, as shown in FIGS. 57-60, the turning tool 242 has a driving component 240 configured to interact with the blocking component 210' as shown in FIG. 50. The driving component 240 has a shape complementary to the slot 226', to make a keyed connection therewith, and is fixed to an elongate sleeve 244 with a lengthwise axis 246. At the axial end of the sleeve 244, remote from the driving component 240, an enlarged head 248 is provided and can be grasped to facilitate manipulation/turning of the sleeve 244 and associated driving component 240 around the axis 246 to allow threaded implantation of the body 214' on the blocking structure 210'.

The turning tool 242 has a slot 249 over its axial length that is wide enough to allow passage therethrough of the suture thread on the suture assembly 18' whereby the driving component 240 can be manipulated to be separated from the suture assembly 18'.

A knot pushing assembly at 250, as seen in FIG. 58, is used to stabilize the knots 24a', 24b' on the exemplary suture assembly 18', as it is usable to stabilize any of the suture knots shown and contemplated, as the suture parts 44a', 44b' are drawn to cinch the knots 24a', 24b'.

The knot pushing assembly 250 has a sleeve 252 with a through opening 254 and an axially facing pushing edge 256 around the through opening 254 to engage the knots 24a', 24b'. By directing the suture parts 44a', 44b' into the opening 256 and advancing the knot pushing assembly 250 along the suture assembly 18' in the direction of the arrow 42 in FIG. 58, the pushing edge 256 can be brought into engagement with the knots 24a', 24b'.

The sleeve 252 has an enlarged head 264 that can be grasped to positively hold the sleeve 252 to brace the knots 24a', 24b'.

Figure 59:
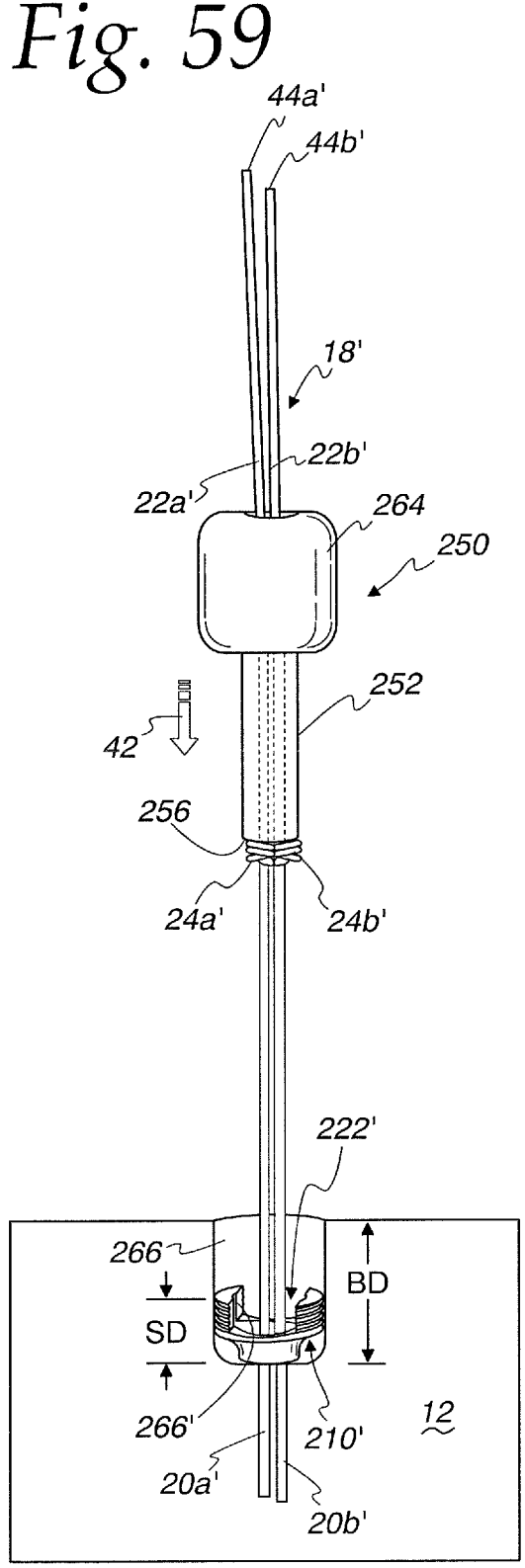
FIG. 59 is a view as in FIG. 58 with the blocking structure having been implanted through the turning tool into the first bone.
Figure 60:
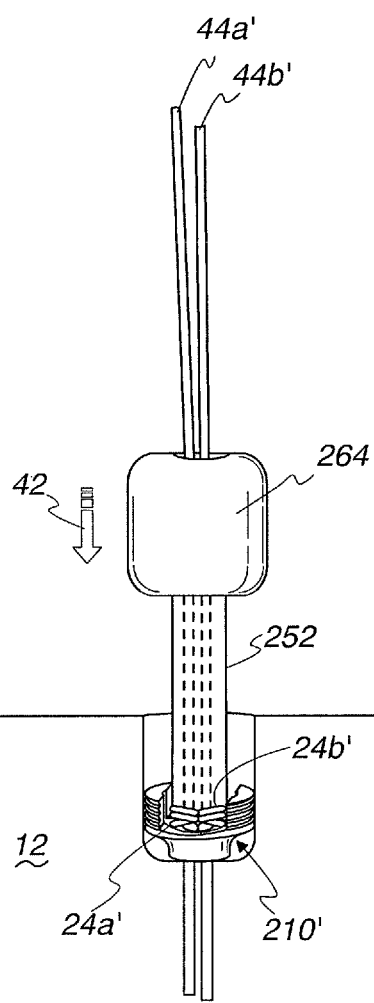
FIG. 60 is a view as in FIG. 59 wherein the knots, stabilized by the knot pushing assembly as in FIG. 59, have been advanced into a receptacle on the implanted blocking structure by reason of restrictable loops on the suture assembly being reduced in size.

In one particular application, as seen in FIGS. 59 and 60, a bore 266 is formed in the first bone 12 to a depth BD. The bore depth BD is substantially greater than the corresponding depth SD of the blocking structure 210'. The blocking structure 210' is implanted using the turning tool 242 with the driving component 240 keyed in the slot 226', as shown in FIG. 57. By then turning the sleeve 244 around the axis 246 through the head 248, the blocking structure 210' is threadably advanced into the bore 266 in which it bottoms out as shown in FIG. 59.

Thereafter, the knot pushing assembly 250, through the pushing edge 256, engages and stabilizes the knots 24a', 24b' as the strand parts 44a', 44b' are drawn away from the first bone and the strands slide through the knots 24a', 24b' as the loops are restricted progressively as shown in FIGS. 59 and 60. The knot pushing assembly 250 moves with the engaged knots 24a', 24b', shifting towards the first bone 12 as the loop restriction progresses until the knots 24a', 24b' abut to the blocking structure 210' and seat in the receptacle 222'. Drawing of the strands 44a', 44b' is controlled to select the size of, and tension on, the restrictable loops 20a', 20b' that maintains the desired relationship between the first bone 12 and the second bone 14.

The blocking structure 210, as noted above, can be made to abut to the knots 24a, 24b, 204 or to accept in the receptacle 222, 222', 222'', 222''', $222^{4'}$, $222^{5'}$ defined thereby, some or all of the volume of the knots 24a', 24b', 204. The system is designed generally so that the knots 24a', 24b', 204 do not protrude so as to potentially cause tissue irritation. Flush or recessed location of the blocking structure 210 may be selected to achieve this end.

Figure 61:
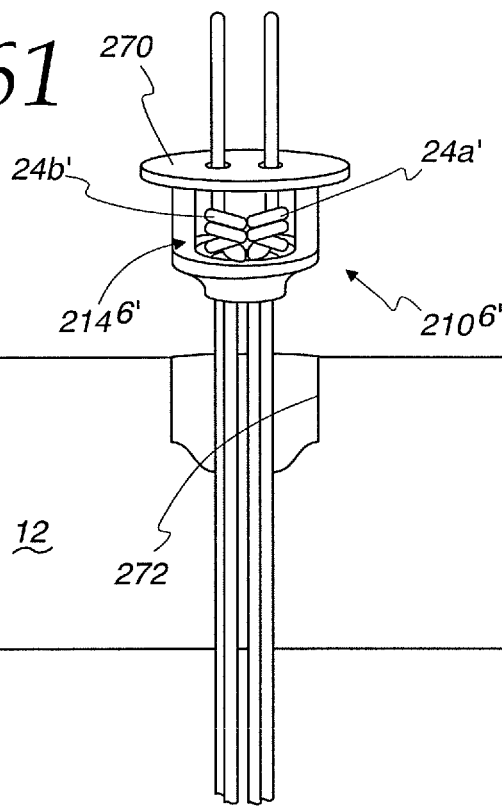
FIG. 61 is a perspective view of a suture assembly showing another form of the inventive blocking structure being advanced into an accommodating bore on the first bone.
Figure 62:
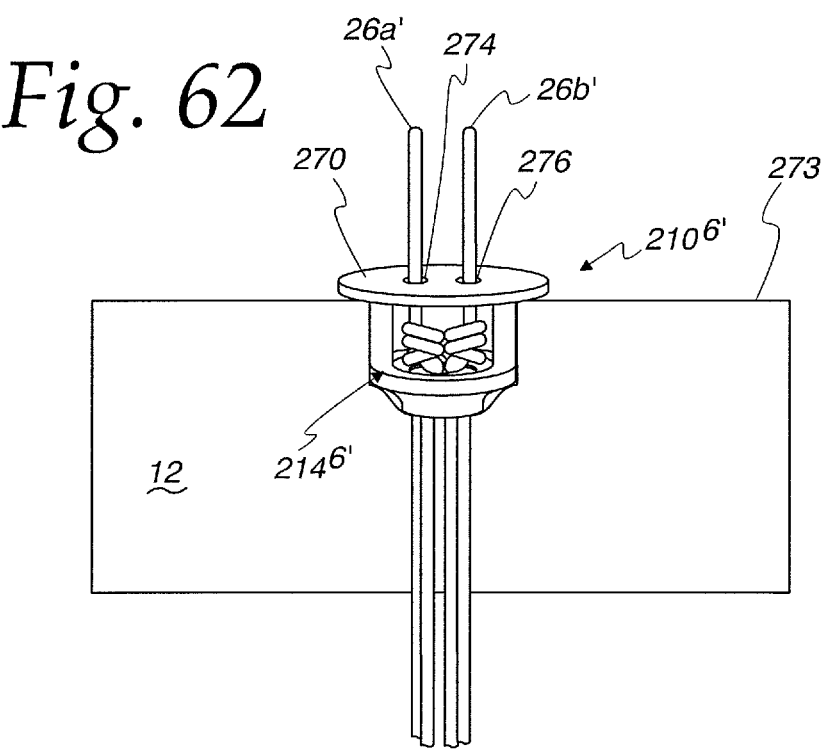
FIG. 62 is a view as in FIG. 61 wherein the blocking structure has been advanced into the bore in a translatory path by restricting the loop size on the associated sutures.

In an alternative system configuration, shown in FIGS. 61 and 62, a blocking structure $210^{6'}$ is shown with a configuration similar to that shown at $210^{5'}$ in FIG. 52. The blocking structure $210^{6'}$ has a body $214^{6'}$ defining a receptacle $222^{6'}$ that accommodates the knots 24a', 24b' beneath a plate 270 that performs the function of the tabs 232 in the embodiment shown in FIG. 52. That is, as seen in FIG. 62, with the first bone 12 drilled to produce a bore 272 that is complementary to the outside shape of the body $214^{6'}$, the plate 270 will abut to an exposed surface 273 of the first bone 12 around the bore 272, to consistently maintain a penetrating depth of the body $214^{6'}$. Whereas the tabs 232 are independent elements spaced from each other, the plate 270 has a continuous shape that fully overlies the diameter of the bore 272. Openings 274, 276 through the plate 270 accommodate the sutures 26a', 26b' and specifically parts thereof that are drawn away from the first bone 12 as the stabilized knots 24a', 24b' shift in the first direction, indicated by the arrow 42, as the size of associated loops is reduced.

Figure 63:
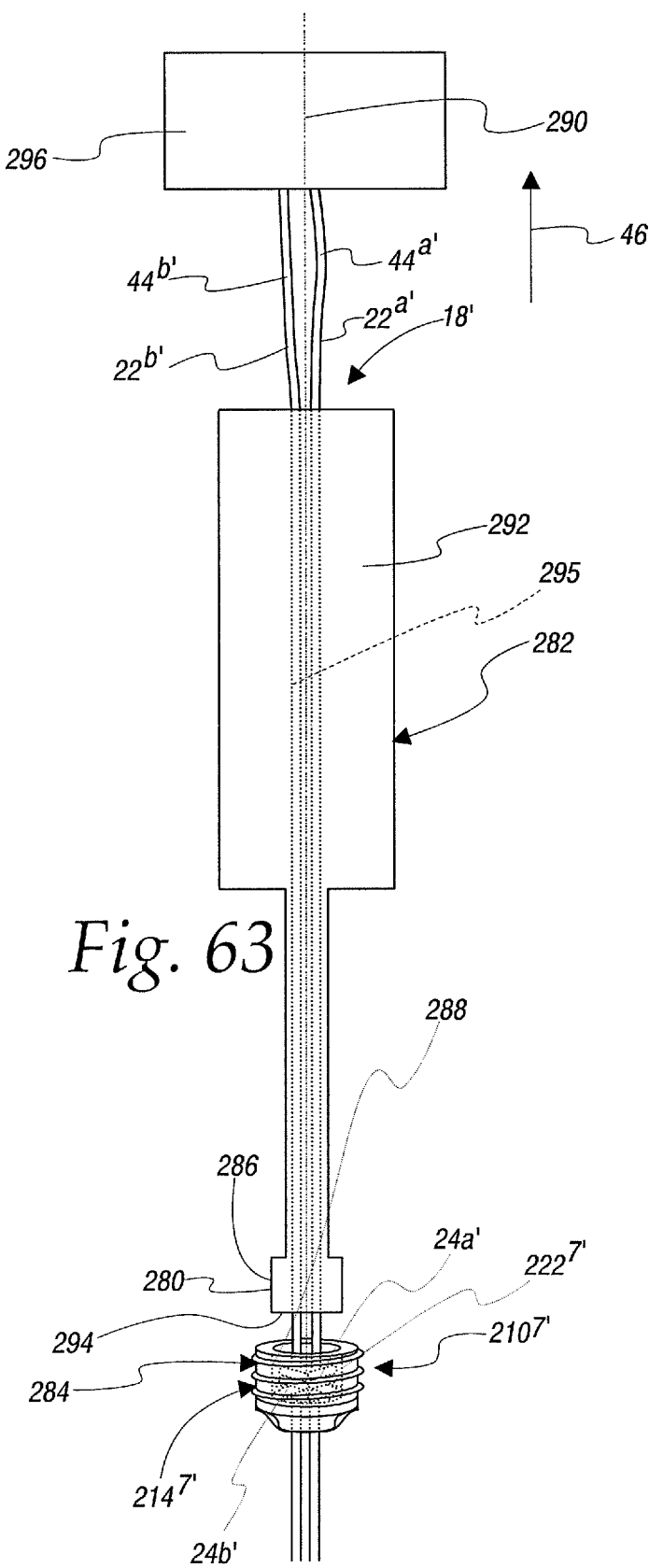
FIG. 63 is a perspective view of a pre-assembled combination of a blocking structure, one form of suture assembly, a tool and graspable handle used together to implant the blocking structure and cinch knots on the suture assembly.

In a still further alternative form of system configuration, as shown in FIG. 63, a blocking structure 210⁷' is used having a body 214⁷', similar to the body 214' as shown in FIGS. 57 and 58. The body 214⁷' defines a receptacle 222⁷' that accommodates the full volume of the knots 24a', 24b'.

The receptacle 222⁷' has sufficient depth to additionally receive a portion of the leading free end 280 of a tool 282 that performs two separate functions—stabilizing the knots 24a', 24b' on the suture assembly 18' as the strand parts 44a', 44b' are drawn in the second direction indicated by the arrow 46, and turning the body 214⁷' to engage threads 284 thereon with the first bone 12.

Figure 64:
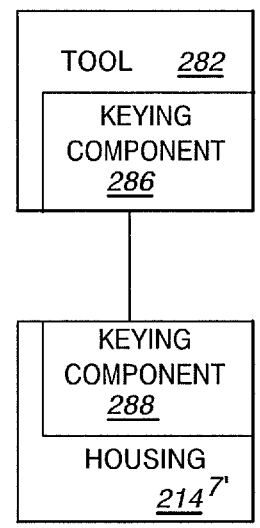
FIG. 64 is a schematic representation of components cooperating between the tool and blocking structure, as in FIG. 63, to allow turning of the blocking structure through the tool.

As shown schematically in FIG. 64, the tool 282 and housing 214⁷' may respectively have fittings/keying components 286, 288 that cooperate with each other to cause the housing 214⁷' to follow movement of the tool 282 as it is turned around its lengthwise axis 290. An enlarged gripping portion 292 is provided to facilitate turning of the tool 282.

The keying components 286, 288 may take virtually an unlimited number of different forms. As just an example, they may be cooperating male and female polygonal shapes. A hexagonal shape or a tori driver configuration might be used.

The free end 280 has a leading edge 294 performing the knot pushing function. The tool 282 has a sleeve with a lengthwise through passage 295 to accommodate the sutures 22a', 22b' that extend through the leading edge 294. The free end 280 is configured so that as the keying component 286 is advanced axially into the receptacle 222⁷' to engage the keying component 288, the edge 294 stabilizes the knots 24a', 24b' within the receptacle 222'.

A graspable handle 296 connects to the strand parts 44a', 44b' to facilitate pulling thereof in the direction of the arrow 46 through the passage 295 with the knots 24a', 24b' stabilized through the tool 282.

Once the body 214⁷' is threaded into place and the strand parts 44a', 44b' drawn to cinch the knots 24a', 24b', the tool 282 can be axially retracted, exposing the strand parts 44a', 44b' adjacent to the first bone 12, whereupon they can be potentially flushly cut to complete the procedure.

With this system, the surgeon can obtain all of the components substantially pre-assembled as shown in FIG. 63. The knots 24a', 24b' are preloaded into the receptacle 222⁷' and the free end 280 of the tool 282 is keyed within the receptacle 222⁷'.

The surgeon can thus push the housing 214⁷' into an accommodating bore in the first bone 12, threadably advance the body 214⁷' into its fully seated position, separate the tool 282, and sever the strands 44a', 44b'.

One exemplary procedure, utilizing the suture assembly 18' and tool 282 is shown in FIGS. 65-74, wherein the first bone 12 is a scaphoid bone and the second bone 14 is a lunate bone.

Figure 65:
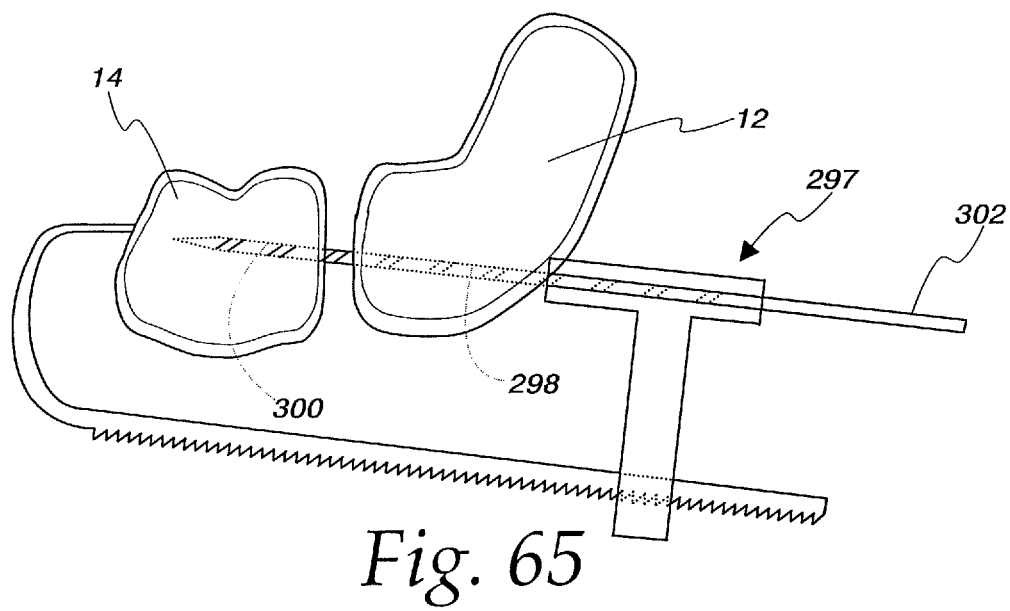

As shown in FIG. 65, a conventional-type guide 297 is employed to produce aligned holes 298, 300, respectively through the scaphoid bone 12 and into the lunate bone 14. A drill component 302 on the guide 297 may alternatively be guided through a conventional-type sleeve (not shown).

Figure 66:
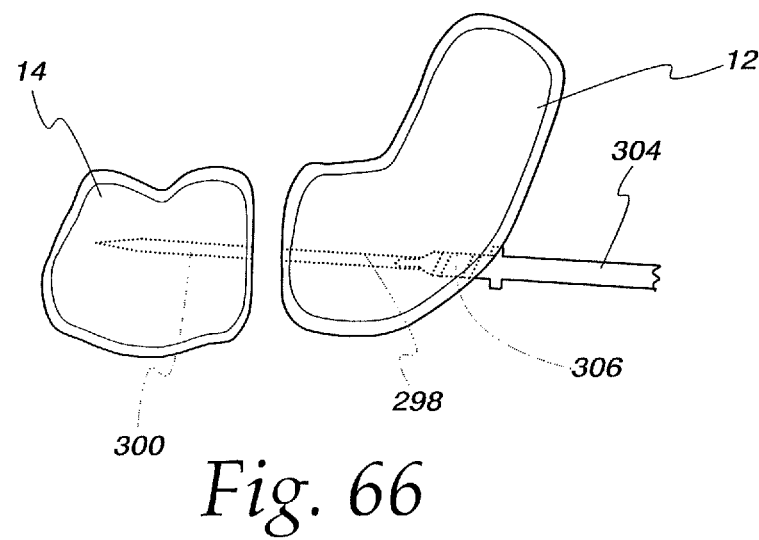

As shown in FIG. 66, with the drill guide 297 and drill component 302 separated, a separate drill component 304 is used to produce a countersunk region at 306 at the entry location to the hole 298.

Alternative forms of components 54⁸', 54⁹', 54¹⁰', that can be anchored in the lunate bone 14, are shown in FIGS. 72-74, successively.

Exemplary component 54⁸' has a shank 308 with threads 310 thereon. The shank 308 has a trailing end at 312 with an eyelet 314 producing a loop through which the suture loops 20a', 20b' extend.

In this embodiment, the shank end 312 has a generally rectangular shape to be engaged by a driver 316 (FIG. 67) having a slotted end 318 that is complementary to the trailing shank end 312. By making a keyed connection between the driver end 318 and the shank end 312, the driver 316 can be grasped, by wrapping a hand around an enlargement 320, and turned around its lengthwise axis 322 to direct the component 54⁸' initially into and thereafter through the hole 298 in the scaphoid 12 and into the hole 300 in the lunate 14, as seen in FIG. 68.

As shown in FIG. 69, the driver 316 is separated from the suture assembly 18' to allow one form of the tool 282⁸' and graspable handle 296⁸', pre-assembled to the suture assembly 18' and a blocking structure 210⁸', to be used to complete the procedure.

As shown in FIGS. 69 and 70, the tool 282⁸' and blocking structure 210⁸' are advanced in the direction of the arrow 42 towards the scaphoid bone 12 and threaded into the hole 298 in the countersunk portion 306 to reside below the exposed surface 324 of the scaphoid bone 12, as shown in FIG. 70.

The leading end 280⁸' on the tool 282⁸' is slightly tapered to have a diameter slightly less than that of the blocking structure 210⁸', whereupon the blocking structure 210⁸' can be advanced into the countersunk portion of the hole 298 without hang-up.

With the knots 24a', 24b' cinched, the tool 282⁸' can be retracted to expose the strand parts 44a', 44b', which can be flushly severed to complete the procedure, as shown in FIG. 71.

In the alternative configuration for the component 54⁹' in FIG. 73, the threaded shank 308⁹' has an eyelet 314⁹' at a leading end 326.

Diametrically opposite grooves 328 (one shown) extend between the eyelet 314⁹' and a trailing end 312⁹' to accommodate the loops 20a', 20b' so that they do not project radially outwardly so that they might be damaged as the anchor 54⁹' is threadably implanted.

The trailing end 312⁹' is shaped to accommodate the aforementioned driver 316, or a driver with another complementary construction. The component 54⁹' otherwise is utilized in the same way as the component 54a'.

The anchoring component 54¹⁰' in FIG. 74 has a shank 308¹⁰' with a hollow construction and a leading end anchoring bar 230 around which the loops 20a', 20b' wrap.

The trailing end 312¹⁰' is configured to cooperate with the driver 316 or other like functioning driver configuration.

While the details of the driver 316 are not shown in the Figures, it is contemplated that a slotted construction can be utilized as shown for the turning tool 242 in FIG. 57, which allows the driver 316 to be changed from an initially fully separated state into an operative position while leaving the suture assembly 18', tool 282⁸', graspable handle 296⁸', and blocking structure 210⁸' pre-assembled and the knots 24a', 24b' pre-formed.

Accordingly, with the pre-assembled components, a surgeon potentially can quickly, simply, and efficiently use the inventive system 16 to reduce and/or maintain separation between the mass/body/bone 12 and mass/body/bone 14. By pre-assembling the components, the surgeon does not have to tie any knots. At the same time, as seen in FIG. 71, the knots 24a', 24b' can be at least partially buried within a bone or implant.

Significantly, the knots 24a', 24b' are cinched by drawing the strand parts 44a', 44b' in a direction substantially parallel to the line of force between the mass/body/bone 12 and mass/body/bone 14 generated through the inventive system 16. This obviates the need to have to conventionally pull strands generally orthogonally to this force line, which is awkward and precludes effective knot formation at any recessed portion of an implant or bone.

Another general form of the system 16, within the generic showing in FIGS. 2 and 3, has a suture assembly 18 with at least a first suture configured to define, either alone or in conjunction with the first body/bone 12, a restrictable loop structure with the suture assembly 18 in an operative state. The restrictable loop structure has at least first and second restrictable sub-loops 20 that cooperatively, either alone or in conjunction with the first body/bone 12, define a combined loop that can be reduced in size to thereby produce a force on the first and second bodies that urges the first and second bodies towards and/or against each other.

As in the various embodiments described above, the first and second restrictable sub-loops 20 respectively made up of first and second loop lengths.

The first loop length has a first sliding portion, with the second loop length having a second sliding portion.

The suture assembly is configured to define at least a first knot that extends around the first and second sliding portions whereupon movement of the first and second sliding portions each within at least one knot in a tightening sliding direction, causes the size of the respective sub-loop to be reduced.

The suture assembly 18 is further configured so that the tensioning of the combined loop, as caused by urging the first and second bodies/banes 12, 14 away from each other with the suture assembly 18 in the operative position, causes the at least one knot to grasp each of the first and second sliding portions with a greater force that opposes enlargement of the sub-loops and thus the combined loop by resisting movement of the first and second sliding portions within the at least one knot in directions opposite to the tightening sliding direction.

Potentially a single knot 24 might be utilized with this basic construction. Each of the first and second loop lengths defines at least a part of the at least first knot.

With the above described structures and methods, it is possible to efficiently utilize operative time and consistently and reliably create secure knots with controlled volumes that can be fully recessed beneath a bone surface.

By at least partially pre-forming knots, the likelihood of an improper knot formation is reduced.

Further, by pre-forming knots that can be shifted into a recessed receptacle as they are cinched, other problems are avoided. Lateral manipulation of strands required to initiate conventional knot formation cannot occur with the knot being built up from within and at the base of a recess or receptacle. As a result, the knots must be fully cinched outside of their associated receptacles. Thereafter, the loops defined by the sutures effectively enlarge as the formed knots are released by the surgeon and allowed to translate into underlying receptacles. Whereas a conventional knot cannot be shifted into a recess while maintaining an established suture tension, the inventive knot, even with a bulky volume, can be effectively shifted into a receptacle to limit or eliminate protrusion without compromising the integrity of the knot or reducing a tension that is selected upon cinching.

Whereas some existing systems, including those with a "knotless" construction, involve multiple components, require complicated cinching steps, and may be difficult for a surgeon to reliably set in a desired state with a desired tension, the present invention permits efficient, simple, and consistent system operation to reliably produce a maintainable force between bodies that can be readily selected and detected by the surgeon.

Figure 75:
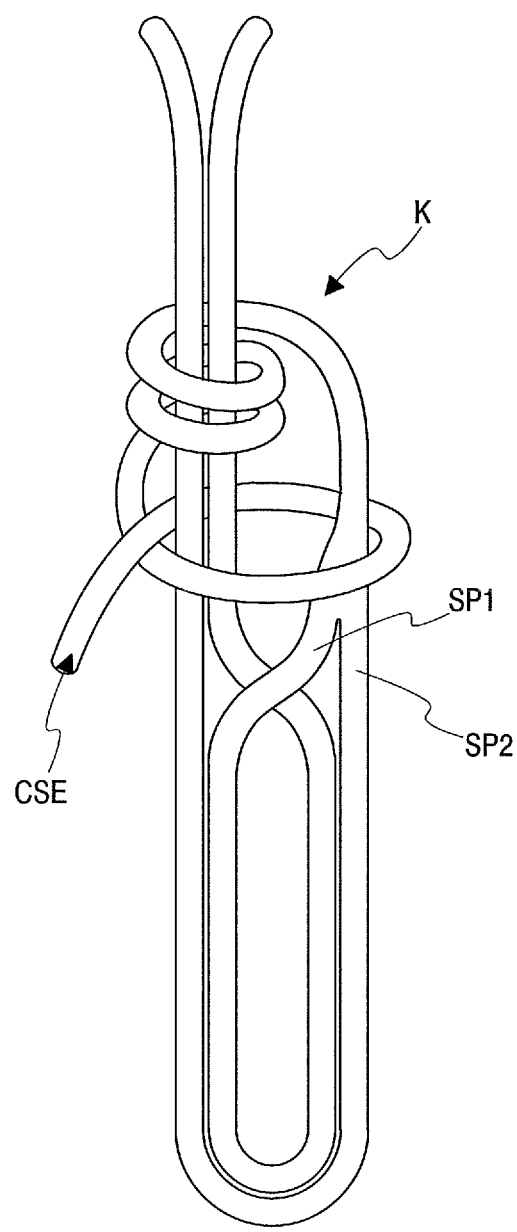
FIG. 75 is a view as in FIG. 47 with the suture assembly modified by strategically joining strand portions to facilitate knot formation.

To facilitate knot formation, parts of the sutures may be strategically joined together to move as one. For example, the suture assembly 18''' in FIG. 47 might be modified as shown in FIG. 75. More specifically, suture free ends SEA, SEB in FIG. 47 might be joined over a discrete length to produce a combined suture free end CSE as shown in FIG. 75. This facilitates manipulation of the suture material during knot formation.

The joining of suture lengths may take place at different locations where suture lengths may remain together during knot formation and cinching. This joining may be effected by any means, such as braiding, sewing, wrapping around the lengths, wrapping the lengths around each other, etc. While not necessary, the joining may also cause the joined suture lengths to assume an effectively reduced volume.

For purposes of simplicity, in the description and claims herein, discrete joined/connected lengths will still be considered to be made up of separate parts. For example, the resulting knot K in FIG. 75 is considered to be a double strand knot even though the separate strand parts SP1, SP2 merge into a composite shape where the strand parts SP1, SP2 may not be distinguishable.

As noted above, discrete strand lengths may be combined elsewhere with different embodiments herein to facilitate knot formation, knot cinching, and overall manipulation of part or all of the particular suture assembly.

The foregoing disclosure of specific embodiments is intended to be illustrative of the broad concepts comprehended by the invention.

The invention claimed is:

1. A system for controlling a relationship between first and second bodies on a person, the system comprising:
   a suture assembly comprising at least a first suture configured to define, either alone or in conjunction with the first body, a restrictable loop structure with the suture assembly in an operative state,
   the restrictable loop structure comprising at least first and second restrictable sub-loops that cooperatively, either alone or in conjunction with the first body, define a first loop that can be reduced in size to thereby be configured to produce a force on the first and second bodies that urges the first and second bodies towards each other,
   the first and second restrictable sub-loops respectively made up of first and second loop lengths,
   the first loop length having a first sliding portion with the second loop length having a second sliding portion,
   the suture assembly configured to define at least one knot that extends around the first and second sliding portions,
   the suture assembly configured so that the first and second sliding portions upon each being moved within the at least one knot in a tightening sliding direction cause a size of a respective sub-loop to be reduced,
   the suture assembly further configured so that tensioning of the first loop, as caused by urging the first and second bodies away from each other with the suture assembly in the operative state, causes separate first and second circumferential lengths of the first loop to be drawn away from the at least one knot, the suture assembly configured so that drawing of each of the first and second circumferential lengths of the first loop away from the at least one knot causes the at least one knot to grasp at least one of the first and second sliding portions with a greater force that opposes enlargement of at least one of the sub-loops and thus an effective size of the first loop by resisting movement of at least one of the first and second sliding portions within the at least one knot in a direction opposite to the tightening sliding direction, wherein the at least one knot comprises first and second knots and the first loop length defines one of the first and second knots and the second loop length defines the other of the first and second knots.

2. A system for controlling a relationship between first and second bodies on a person, the system comprising:

a suture assembly comprising at least a first suture configured to define, either alone or in conjunction with the first body, a restrictable loop structure with the suture assembly in an operative state, the restrictable loop structure comprising at least first and second restrictable sub-loops that cooperatively, either alone or in conjunction with the first body, define a first loop that can be reduced in size to thereby be configured to produce a force on the first and second bodies that urges the first and second bodies towards each other, the first and second restrictable sub-loops respectively made up of first and second loop lengths, the first loop length having a first sliding portion with the second loop length having a second sliding portion, the suture assembly configured to define at least one knot that extends around the first and second sliding portions, the suture assembly configured so that the first and second sliding portions upon each being moved within the at least one knot in a tightening sliding direction cause a size of a respective sub-loop to be reduced, the suture assembly further configured so that tensioning of the first loop, as caused by urging the first and second bodies away from each other with the suture assembly in the operative state, causes separate first and second circumferential lengths of the first loop to be drawn away from the at least one knot, the suture assembly configured so that drawing of each of the first and second circumferential lengths of the first loop away from the at least one knot causes the at least one knot to grasp at least one of the first and second sliding portions with a greater force that opposes enlargement of at least one of the sub-loops and thus an effective size of the first loop by resisting movement of at least one of the first and second sliding portions within the at least one knot in a direction opposite to the lightening sliding direction, wherein the first and second restrictable sub-loops are made up of the first suture and a separate second suture.

3. A system for controlling a relationship between first and second bodies on a person, the system comprising:

a suture assembly comprising at least a first suture configured to define, either alone or in conjunction with the first body, a restrictable loop structure with the suture assembly in an operative state, the restrictable loop structure comprising at least first and second restrictable sub-loops that cooperatively, either alone or in conjunction with the first body, define a first loop that can be reduced in size to thereby be configured to produce a force on the first and second bodies that urges the first and second bodies towards each other, the first and second restrictable sub-loops respectively made up of first and second loop lengths, the first loop length having a first sliding portion with the second loop length having a second sliding portion, the suture assembly configured to define at least one knot that extends around the first and second sliding portions, the suture assembly configured so that the first and second sliding portions upon each being moved within the at least one knot in a tightening sliding direction cause a size of a respective sub-loop to be reduced, the suture assembly further configured so that tensioning of the first loop, as caused by urging the first and second bodies away from each other with the suture assembly in the operative state, causes separate first and second circumferential lengths of the first loop to be drawn away from the at least one knot, the suture assembly configured so that drawing of each of the first and second circumferential lengths of the first loop away from the at least one knot causes the at least one knot to grasp at least one of the first and second sliding portions with a greater force that opposes enlargement of at least one of the sub-loops and thus an effective size of the first loop by resisting movement of at least one of the first and second sliding portions within the at least one knot in a direction opposite to the tightening sliding direction, wherein the suture assembly comprises the first suture and a second suture and with the suture assembly in the operative state the first suture is formed with a configuration that is the same as a configuration of the second suture.

4. A system for controlling a relationship between first and second bodies on a person, the system comprising:

a suture assembly comprising at least a first suture configured to define, either alone or in conjunction with the first body, a restrictable loop structure with the suture assembly in an operative state, the restrictable loop structure comprising at least first and second restrictable sub-loops that cooperatively, either alone or in conjunction with the first body, define a first loop that can be reduced in size to thereby be configured to produce a force on the first and second bodies that urges the first and second bodies towards each other, the first and second restrictable sub-loops respectively made up of first and second loop lengths, the first loop length having a first sliding portion with the second loop length having a second sliding portion, the suture assembly configured to define at least one knot that extends around the first and second sliding portions, the suture assembly configured so that the first and second sliding portions upon each being moved within the at least one knot in a tightening sliding direction cause a size of a respective sub-loop to be reduced, the suture assembly further configured so that tensioning of the first loop, as caused by urging the first and second bodies away from each other with the suture assembly in the operative state, causes separate first and second circumferential lengths of the first loop to be drawn away from the at least one knot, the suture assembly configured so that drawing of each of the first and second circumferential lengths of the first loop away from the at least one knot causes the at least one knot to grasp at least one of the first and second sliding portions with a greater, force that opposes enlargement of at least one of the sub-loops and thus an effective size of the first loop by resisting movement of at least one of the first and second sliding portions within the at least one knot in a direction opposite to the tightening sliding direction, wherein the at least one knot comprises first and second knots, wherein the suture assembly comprises the first suture and a second suture and the first and second sutures have first and second strand lengths that are maintained together and formed in the same manner to produce the first and second knots so that the first and second knots are combined to produce a double strand knot with the suture assembly in the operative state.

5. A system for controlling a relationship between first and second bodies on a person, the system comprising:

a suture assembly comprising at least a first suture, configured to define, either alone or in conjunction with the first body, a restrictable loop structure with the suture assembly in an operative state, the restrictable loop structure comprising at least first and second restrictable sub-loops that cooperatively, either alone or in conjunction with the first body, define a first loop that can be reduced in size to thereby be configured to produce a force on the first and second bodies that urges the first and second bodies towards each other, the first and second restrictable sub-loops respectively made up of first and second loop lengths, the first loop length having a first sliding portion with the second loop length having a second sliding portion, the suture assembly configured to define at least one knot that extends around the first and second sliding portions, the suture assembly configured so that the first and second sliding portions upon each being moved within the at least one knot in a tightening sliding direction cause a size of a respective sub-loop to be reduced, the suture assembly further configured so that tensioning of the first loop, as caused by urging the first and second bodies away from each other with the suture assembly in the operative state, causes separate first and second circumferential lengths of the first loop to be drawn away from the at least one knot, the suture assembly configured so that drawing of each of the first and second circumferential lengths of the first loop away from the at least one knot causes the at least one knot to grasp at least one of the first and second sliding portions with a greater force that opposes enlargement of at least one of the sub-loops and thus an effective size of the first loop by resisting movement of at least one of the first and second sliding portions within the at least one knot in a direction opposite to the tightening sliding direction, wherein the at least one knot comprises first and second knots that each is one of: a) a half hitch; b) a rolling hitch; c) an adjustable bend; d) a midshipman's hitch; and e) an adjustable hitch knot.

6. A system for controlling a relationship between first and second bodies on a person, the system comprising:

a suture assembly comprising at least a first suture configured to define, either alone or in conjunction with the first body, a restrictable loop structure with the suture assembly in an operative state, the restrictable loop structure comprising at least first and second restrictable sub-loops that cooperatively, either alone or in conjunction with the first body, define a first loop, that can be reduced in size to thereby be configured to produce a force on the first and second bodies that urges the first and second bodies towards each other, the first and second restrictable sub-loops respectively made up of first and second loop lengths, the first loop length having a first sliding portion with the second loop length having a second sliding portion, the suture assembly configured to define at least one knot that extends around the first and second sliding portions, the suture assembly configured so that the first and second sliding portions upon each being moved within the at least one knot in a tightening sliding direction cause a size of a respective sub-loop to be reduced, the suture assembly further configured so that tensioning of the first loop, as caused by urging the first and second bodies away from each other with the suture assembly in the operative state, causes separate first and second circumferential lengths of the first loop to be drawn away from the at least one knot, the suture assembly configured so that drawing of each of the first and second circumferential lengths of the first loop away from the at least one knot causes the at least one knot to grasp at least one of the first and second sliding portions with a greater force that opposes enlargement of at least one of the sub-loops and thus an effective size of the first loop by resisting movement of at least one of the first and second sliding portions within the at least one knot in a direction opposite to the tightening sliding direction, wherein the at least one knot comprises first and second knots, wherein the suture assembly comprises at least one component that is configured to reside between each of the first and second knots and the first body with the suture assembly in the operative state, the at least one component configured to block advancing of the first and second knots through the at least one component.

7. The system for controlling a relationship between first and second bodies on a person according to claim 6, wherein the suture assembly further comprises at least a second component that is configured to reside between portions of the restrictable sub-loops and the second body.

8. A system for controlling a relationship between first and second bodies on a person, the system comprising:

a suture assembly comprising at least a first suture configured to define, either alone or in conjunction with the first body, a restrictable loop structure with the suture assembly in an operative state, the restrictable loop structure comprising at least first and second restrictable sub-loops that cooperatively, either alone or in conjunction with the first body, define a first loop that can be reduced in size to thereby be configured to produce a force on the first and second bodies that urges the first and second bodies towards each other, the first and second restrictable sub-loops respectively made up of first and second loop lengths, the first loop length having a first sliding portion with the second loop length having a second sliding portion, the suture assembly configured to define at least one knot that extends around the first and second sliding portions, the suture assembly configured so that the first and second sliding portions upon each being moved within the at least one knot in a tightening sliding direction cause a size of a respective sub-loop to be reduced, the suture assembly further configured so that tensioning of the first loop, as caused by urging the first and second bodies away from each other with the suture assembly in the operative state, causes separate first and second circumferential lengths of the first loop to be drawn away from the at least one knot, the suture assembly configured so that drawing of each of the first and second circumferential lengths of the first loop away from the at least one knot causes the at least one knot to grasp at least one of the first and second sliding portions with a greater force that opposes enlargement of at least one of the sub-loops and thus an effective size of the first loop by resisting movement of at least one of the first and second sliding portions within the at least one knot in a direction opposite to the tightening sliding direction, wherein with the suture assembly in the operative state the first and second restrictable sub-loops extend each through the other.

9. A system for controlling a relationship between first and second bodies on a person, the system comprising:

a suture assembly comprising at least a first suture configured to define, either alone or in conjunction with the first body, a restrictable loop structure with the suture assembly in an operative state, the restrictable loop structure comprising at least first and second restrictable sub-loops that cooperatively, either alone or in conjunction with the first body, define a first loop that can be reduced in size to thereby be configured to produce a force on the first and second bodies that urges the first and second bodies towards each other, the first and second restrictable sub-loops respectively made up of first and second loop lengths, the first loop length having a first sliding portion with the second loop length having a second sliding portion, the suture assembly configured to define at least one knot that extends around the first and second sliding portions, the suture assembly configured so that the first and second sliding portions upon each being moved within the at least one knot in a tightening sliding direction cause a size of a respective sub-loop to be reduced, the suture assembly further configured so that tensioning of the first loop, as caused by urging the first and second bodies away from each other with the suture assembly in the operative state, causes separate first and second circumferential lengths of the first loop to be drawn away from the at least one knot, the suture assembly configured so that drawing of each of the first and second circumferential lengths of the first loop away from the at least one knot causes the at least one knot to grasp at least one of the first and second sliding portions with a greater force that opposes enlargement of at least one of the sub-loops and thus an effective size of the first loop by resisting movement of at least one of the first and second sliding portions within the at least one knot in a direction opposite to the tightening sliding direction, wherein the suture assembly comprising first and second strands that with the suture assembly in the operative state are configured to be drawn away from the first body to reduce sizes of the first and second restrictable sub-loops, wherein lengths of the at least first suture on the first and second restrictable sub-loops move in opposite directions along a length of the first loop as the first and second strands are drawn away from the first body, wherein the at least one knot comprises first and second knots, wherein the system is provided in combination with a knot pusher that is configured to engage and stabilize at least one of the first and second knots as the first and second strands are drawn away from the first body to thereby reduce sizes of the first and second restrictable sub-loops.

10. A system for controlling a relationship between first and second bodies on a person, the system comprising:

a suture assembly comprising at least a first suture configured to define, either alone or in conjunction with the first body, a restrictable loop structure with the suture assembly in an operative state, the restrictable loop structure comprising at least first and second restrictable sub-loops that cooperatively, either alone or in conjunction with the first body, define a first loop that can be reduced in size to thereby be configured to produce a force on the first and second bodies that urges the first and second bodies towards each other, the first and second restrictable sub-loops respectively made up of first and second loop lengths, the first loop length having a first sliding portion with the second loop length having a second sliding portion, the suture assembly configured to define at least one knot that extends around the first and second sliding portions, the suture assembly configured so that the first and second sliding portions upon each being moved within the at least one knot in a tightening sliding direction cause a size of a respective sub-loop to be reduced, the suture assembly further configured so that tensioning of the first loop, as caused by urging the first and second bodies away from each other with the suture assembly in the operative state, causes separate first and second circumferential lengths of the first loop to be drawn away from the at least one knot, the suture assembly configured so that drawing of each of the first and second circumferential lengths of the first loop away from the at least one knot causes the at least one knot to grasp at least one of the first and second sliding portions with a greater force that opposes enlargement of at least one of the sub-loops and thus an effective size of the first loop by resisting movement of at least one of the first and second sliding portions within the at least one knot in a direction opposite to the tightening sliding direction, wherein the first and second bodies are first and second bones, wherein the at least one knot comprises first and second knots, wherein the suture assembly comprises at least one component configured to abut to the first bone, the at least one component defining a surface that abuts to each of the first and second knots with the suture assembly in the operative state to thereby block advancing of the first and second knots through the at least one component.

11. The system for controlling a relationship between first and second bodies on a person according to claim 10 wherein the at least one component defines a receptacle configured to receive at least a portion of at least one of the first and second knots.

12. The system for controlling a relationship between first and second bodies on a person according to claim 10 wherein the at least one component defines a receptacle to receive a majority of the first and second knots.

13. The system for controlling a relationship between first and second bodies on a person according to claim 10 wherein the at least one component is threaded to engage one of: a) the first bone; and b) a plate connected to the first bone.

14. The system for controlling a relationship between first and second bodies on a person according to claim 13 wherein the at least one component has a fitting to accommodate a turning tool.

15. The system for controlling a relationship between first and second bodies on a person according to claim 14 in combination with a turning tool with a driving component configured to make a keyed connection with the fitting on the at least one component.

16. The system for controlling a relationship between first and second bodies on a person according to claim 15 wherein the turning tool further comprises an elongate sleeve with a lengthwise axis.

17. The system for controlling a relationship between first and second bodies on a person according to claim 10 wherein the at least one component defines a receptacle to receive substantially an entirety of the first and second knots.

18. A system for controlling a relationship between first and second bodies on a person, the system comprising:
a suture assembly comprising at least a first suture configured to define, either alone or in conjunction with the first body, a restrictable loop structure with the suture assembly in an operative state,
the restrictable loop structure comprising at least first and second restrictable sub-loops that cooperatively, either alone or in conjunction with the first body, define a first loop that can be reduced in size to thereby be configured to produce a force on the first and second bodies that urges the first and second bodies towards each other,
the first and second restrictable sub-loops respectively made up of first and second loop lengths,
the first loop length having a first sliding portion with the second loop length having a second sliding portion,
the suture assembly configured to define at least one knot that extends around the first and second sliding portions,
the suture assembly configured so that the first and second sliding portions upon each being moved within the at least one knot in a tightening sliding direction cause a size of a respective sub-loop to be reduced,
the suture assembly further configured so that tensioning of the first loop, as caused by urging the first and second bodies away from each other with the suture assembly in the operative state, causes separate first and second circumferential lengths of the first loop to be drawn away from the at least one knot,
the suture assembly configured so that drawing of each of the first and second circumferential lengths of the first loop away from the at least one knot causes the at least one knot to grasp at least one of the first and second sliding portions with a greater force that opposes enlargement of at least one of the sub-loops and thus an effective size of the first loop by resisting movement of at least one of the first and second sliding portions within the at least one knot in a direction opposite to the tightening sliding direction,
wherein the first and second bodies are first and second bones,
wherein the at least one knot comprises first and second knots,
wherein the system further comprises a plate configured to be fixed to the first bone to stabilize parts of the first bone near a fracture, wherein the suture assembly further comprises a component that is configured to be fixed to the plate and define a surface that abuts to at least one of the first and second knots with the suture assembly in the operative state to thereby block advancing of the first and second knots through the first bone.

19. The system for controlling a relationship between first and second bodies on a person according to claim 18 wherein the component is configured to be anchored within the first bone with the suture assembly in the operative state.

20. A system for controlling a relationship between first and second bodies on a person, the system comprising:
a suture assembly comprising at least a first suture configured to define, either alone or in conjunction with the first body, a restrictable loop structure with the suture assembly in an operative state,
the restrictable loop structure comprising at least first and second restrictable sub-loops that cooperatively, either alone or in conjunction with the first body, define a first loop that can be reduced in size to thereby be configured to produce a force on the first and second bodies that urges the first and second bodies towards each other,
the first and second restrictable sub-loops respectively made up of first and second loop lengths,
the first loop length having a first sliding portion with the second loop length, having a second sliding portion,
the suture assembly configured to define at least one knot that extends around the first and second sliding portions,
the suture assembly configured so that the first and second sliding portions upon each being moved within the at least one knot in a tightening sliding direction cause a size of a respective sub-loop to be reduced,
the suture assembly further configured so that tensioning of the first loop, as caused by urging the first and second bodies away from each other with the suture assembly in the operative state, causes separate first and second circumferential lengths of the first loop to be drawn away from the at least one knot,
the suture assembly configured so that drawing of each of the first and second circumferential lengths of the first loop away from the at least one knot causes the at least one knot to grasp at least one of the first and second sliding portions with a greater force that opposes enlargement of at least one of the sub-loops and thus an effective size of the first loop by resisting movement of at least one of the first and second sliding portions within the at least one knot in a direction opposite to the tightening sliding direction,
wherein the at least one knot comprises first and second knots,
wherein tension applied to the first and second circumferential lengths in a direction away from each of the first and second knots causes each of the first and second knots to reconfigure a respective length of the at least first suture that it extends around to assume a non-linear shape resulting in increased resistance to sliding.

21. A method of controlling a relationship between first and second bodies each in the form of a bone on a person, the method comprising the steps of:
  obtaining a system as recited in claim 1;
  with the suture assembly in a starting state, directing portions of the first and second restrictable sub-loops through at least one passage in the first bone;
  engaging the first and second sub-loops either directly or indirectly with the second bone;
  with the first and second sub-loops engaged with the second bone, simultaneously drawing parts of the at least first suture away from the first bone while stabilizing the at least one knot to thereby produce a tension on the first and second restrictable sub-loops selected to maintain a desired relationship between the first and second bones.

22. The method of controlling a relationship between first and second bodies on a person according to claim 21 wherein the system further comprises at least one component that resides between the at least one knot and the first bone with the suture assembly in the operative state, the at least one component configured to block advancing of the at least one knot through the at least one passage, and the step of drawing parts of the at least first suture while stabilizing the at least one knot comprises causing the at least one knot to bear against the at least one component.

23. The method of controlling a relationship between first and second bodies on a person according to claim 22 wherein the at least one component has a receptacle and the step of drawing parts of the at least first suture while stabilizing the at least one knot comprises causing at least part of the at least one knot to reside in the receptacle as the parts of the at least first suture are being drawn to reduce the sizes of the first and second restrictable sub-loops.

24. The method of controlling a relationship between first and second bodies on a person according to claim 22 wherein the at least one component has a receptacle and the step of drawing parts of the at least first suture while stabilizing the at least one knot comprises causing substantially an entirety of the at least one knot to reside in the receptacle as the parts of the at least first suture are being drawn.

25. The method of controlling a relationship between first and second bodies on a person according to claim 22 further comprising the step of recessing the at least one component in the first bone.

26. The method of controlling a relationship between first and second bodies on a person according to claim 21 wherein the at least one knot is configured so that the at least one knot is blocked from moving through the at least one passage in the first bone.

* * * * *

UNITED STATES PATENT AND TRADEMARK OFFICE
CERTIFICATE OF CORRECTION

PATENT NO. : 10,758,224 B2
APPLICATION NO. : 15/470321
DATED : September 1, 2020
INVENTOR(S) : Robert Medoff Page 1 of 2

It is certified that error appears in the above-identified patent and that said Letters Patent is hereby corrected as shown below:

On the Title Page

Item (54) and in the Specification, Column 1 Lines 1-3 should read:
SYSTEM AND METHOD FOR CONTROLLING A RELATIONSHIP BETWEEN FIRST AND SECOND BODIES ON A PERSON In the Claims Column 27 Lines 16-57 should read:
2. A system for controlling a relationship between first and second bodies on a person, the system comprising:
    a suture assembly comprising at least a first suture configured to define, either alone or in conjunction with the first body, a restrictable loop structure with the suture assembly in an operative state,
    the restrictable loop structure comprising at least first and second restrictable sub-loops that cooperatively, either alone or in conjunction with the first body, define a first loop that can be reduced in size to thereby be configured to produce a force on the first and second bodies that urges the first and second bodies towards each other,
    the first and second restrictable sub-loops respectively made up of first and second loop lengths,
    the first loop length having a first sliding portion with the second loop length having a second sliding portion,
    the suture assembly configured to define at least one knot that extends around the first and second sliding portions,
    the suture assembly configured so that the first and second sliding portions upon each being moved within the at least one knot in a tightening sliding direction cause a size of a respective sub-loop to be reduced,
    the suture assembly further configured so that tensioning of the first loop, as caused by urging Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office* the first and second bodies away from each other with the suture assembly in the operative state, causes separate first and second circumferential lengths of the first loop to be drawn away from the at least one knot, the suture assembly configured so that drawing of each of the first and second circumferential lengths of the first loop away from the at least one knot causes the at least one knot to grasp at least one of the first and second sliding portions with a greater force that opposes enlargement of at least one of the sub-loops and thus an effective size of the first loop by resisting movement of at least one of the first and second sliding portions within the at least one knot in a direction opposite to the tightening sliding direction, wherein the first and second restrictable sub-loops are made up of the first suture and a separate second suture.